(12) United States Patent
Noda et al.

(10) Patent No.: US 7,553,535 B2
(45) Date of Patent: Jun. 30, 2009

(54) NONWOVEN FABRIC

(75) Inventors: Yuki Noda, Kagawa (JP); Hideyuki Ishikawa, Kagawa (JP); Satoshi Mizutani, Kagawa (JP); Akihiro Kimura, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 11/755,537

(22) Filed: May 30, 2007

(65) Prior Publication Data

US 2007/0298220 A1 Dec. 27, 2007

(30) Foreign Application Priority Data

Jun. 23, 2006 (JP) ............................. 2006-174505
Sep. 29, 2006 (JP) ............................. 2006-270105

(51) Int. Cl.
| | |
|---|---|
| B32B 3/10 | (2006.01) |
| B32B 3/00 | (2006.01) |
| B32B 5/06 | (2006.01) |
| B32B 5/14 | (2006.01) |
| B32B 5/26 | (2006.01) |
| B32B 7/08 | (2006.01) |
| D04H 1/00 | (2006.01) |
| D04H 3/00 | (2006.01) |
| D04H 5/00 | (2006.01) |
| D04H 13/00 | (2006.01) |

(52) U.S. Cl. ........................ 428/156; 428/131; 428/137; 428/167; 428/170; 428/171; 428/172; 442/327; 442/387

(58) Field of Classification Search ................ 428/156, 428/167, 170, 171, 172, 131, 137, 188; 442/327, 442/387
See application file for complete search history.

(56) References Cited

U.S. PATENT DOCUMENTS

| | | | |
|---|---|---|---|
| 4,016,319 A | | 4/1977 | Marshall |
| 5,618,610 A | * | 4/1997 | Tomita et al. ............... 428/152 |
| 6,096,016 A | | 8/2000 | Tsuji et al. |
| 6,451,718 B1 | * | 9/2002 | Yamada et al. ............... 442/149 |
| 6,641,902 B1 | | 11/2003 | Kobayashi et al. |
| 6,867,156 B1 | * | 3/2005 | White et al. ................. 442/334 |
| 6,936,333 B2 | | 8/2005 | Shizuno et al. |

FOREIGN PATENT DOCUMENTS

| | | |
|---|---|---|
| JP | 2169718 A | 6/1990 |
| JP | 02-229255 A | 9/1990 |
| JP | 05-222657 A | 8/1993 |

(Continued)

OTHER PUBLICATIONS

International Search Report of PCT/JP2007/060543 issued Jul. 10, 2007.
International Search Report of PCT/JP2007/061601 issued Aug. 7, 2007.
International Search Report of PCT/JP2007/061445 issued Jul. 31, 2007.

*Primary Examiner*—Jennifer McNeil
*Assistant Examiner*—Catherine Simone
(74) *Attorney, Agent, or Firm*—Lowe Hauptman Ham & Berner, LLP

(57) ABSTRACT

Nonwoven fabric including concaves and convexes, and at least a fiber basis weight which is adjusted, and its manufacturing method are provided. The nonwoven fabric 110 is formed into a substantially sheet-like shape of predetermined thickness and its fiber basis weight is adjusted by directing a fluid, mainly consisting of gas, to a fiber web 100, the fibers of which have a high degree of freedom to move. The nonwoven fabric 110 includes a plurality of groove portions 1, which are low basis weight portions, and a plurality of convex portions 2, which are high basis weight portions, that are continuously formed along the groove portions 1 and are adjacent to each of the plurality of groove portions 1. The Fiber basis weights of the plurality of groove portions 1 are less than those of the plurality of convex portions 2.

19 Claims, 19 Drawing Sheets

FOREIGN PATENT DOCUMENTS

| | | |
|---|---|---|
| JP | 08-060509 A | 3/1996 |
| JP | 2543597 B2 | 7/1996 |
| JP | 08-216310 A | 8/1996 |
| JP | 2747364 B2 | 2/1998 |
| JP | 2002-030557 A | 1/2002 |
| JP | 2002-136547 A | 5/2002 |
| JP | 2002-249965 A | 9/2002 |
| JP | 3587831 B2 | 8/2004 |
| JP | 2004-344443 A | 12/2004 |
| JP | 2005-097782 A | 4/2005 |

* cited by examiner

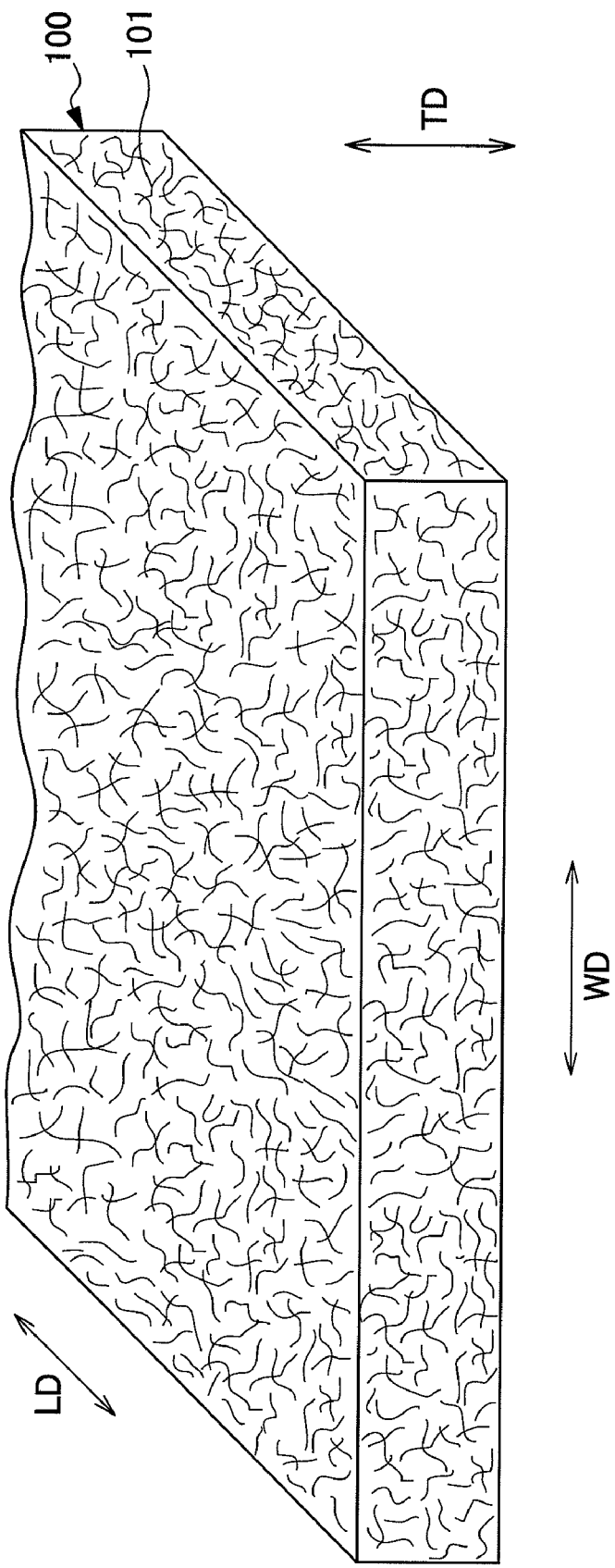

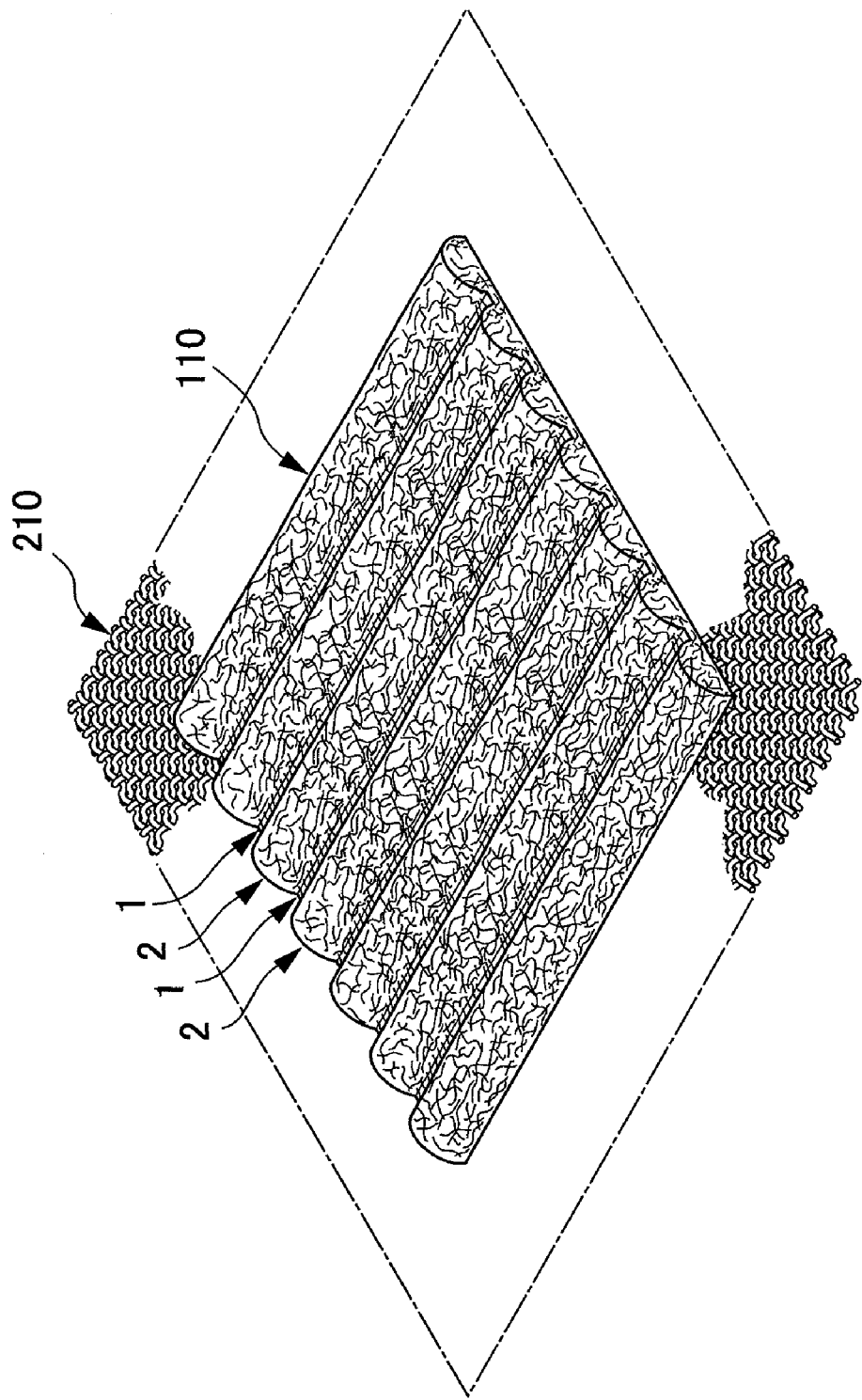

NONWOVEN FABRIC

This application claims benefits of priority based on Japanese Patent Application No. 2006-174505, filed on 23 Jun. 2006 and Japanese Patent Application No. 2006-270105, filed on 29 Sep. 2006, contents of which are incorporated herein by reference.

BACKGROUND OF THE INVENTION

1. Field of the Invention

The present invention relates to nonwoven fabric.

2. Related Art

Conventionally, nonwoven fabrics are used in a variety of fields, for example, sanitary products such as disposable diaper and sanitary napkin, cleaning products such as wipers and medical products such as masks. Such nonwoven fabrics are used in many different fields, but when actually used in products of each of those fields, it is necessary that the nonwoven fabric are manufactured with the properties and structures appropriate for their intended use.

For example, nonwoven fabric can be manufactured by forming a fiber layer (fiber web) either by a dry method or a wet method, and then bonding the fibers of the fiber layer together by a chemical bond method or a thermal bond method. Methods for bonding the fibers that form the fiber layer includes a method of externally applying a physical force to the fiber layer where a plurality of needles are repeatedly inserted into the fiber layer or a method of applying a physical force where aqueous steam is injected into the fiber layer.

However, according to these methods the fibers are only entangled with each other and the orientation or arrangement of the fibers of the fiber layer or the shape of the fiber layer is not adjusted. In other words, these methods only manufacture a simple sheet-like nonwoven fabric.

For example, in the case of nonwoven fabric used as a top sheet of an absorbent article, when the liquid of an excrement is absorbed during use of the absorbent article, a nonwoven fabric having irregular portions is preferably used in order to maintain or improve the positive feeling of the article when it comes into contact with the skin of the user. Japanese Patent Publication No. 3587831 (hereinafter referred to as Patent Document 1) discloses a nonwoven fabric in which a plurality of finer layers, including fibers of different heat shrinkability, are stacked together to be thermally bonded, and irregular portions are formed on a surface by heat contraction of at least one of the fiber layers, and its manufacturing method.

In the case of the nonwoven fabric disclosed in Patent Document 1, when the irregular portions are formed in the nonwoven fabric, the plurality of fiber layers are stacked together to integrate the fibers of the fibers layers by thermal bonding, and thus the fiber density increases in areas where the fibers have been thermally bonded. As a result, permeation of a predetermined liquid of an excrement through an absorbent layer becomes difficult. In addition, when the thermally bonded area is formed into a film, rapid downward permeation of the predetermined liquid excrement also becomes more difficult.

The nonwoven fabric disclosed in the Patent Document 1 is manufactured by stacking a second fiber layer made of a thermal non-contractive fiber on one or both surfaces of a first fiber layer consisting of a fiber including a thermally contracted thermal contractive fiber. The fibers are integrated by a large number of thermally bound portions. In the thermally bound portions, the second fiber layer projects by thermal contraction of the first fiber layer to form portions of varying height.

In other words, as a plurality of fiber layers that differ from one another in their nature are necessary to form irregular portions on the surface of the nonwoven fabric, the manufacturing process is complex. When the first and second fiber layers are peeled off during thermal contraction of the thermal contractive fiber, the second fiber layer cannot form a convex portion. Thus, to prevent the first and second fiber layers from peeling, the thermally bonded portions must be securely bound. However in this situation the density of the thermally bonded portions increases, a film is formed, and rapid permeation of the liquid of the excrement becomes difficult. These are the problems to be solved by the present invention.

SUMMARY OF THE INVENTION

The present invention has been developed to solve the aforementioned problems, and it is an object of the invention to provide a nonwoven fabric which facilitates rapid permeation of a liquid and at least the fiber basis weight is adjusted.

The inventors have discovered that at least the basis weight of a fiber web can be adjusted by blowing a gas from the upper side to a fiber web that is supported from the lower side by a predetermined air permeable support member so as to move fibers forming the fiber web, thereby completing the present invention.

According to a first embodiment of the present invention a nonwoven fabric includes a plurality of low basis weight portions formed in a first direction by blowing a fluid, mainly consisting of gas, to a fiber assembly; and a plurality of high basis weight portions formed to be adjacent to and along each of the plurality of low basis weight portions, in which the fiber basis weight of each of the plurality of low basis weight portions is less than the fiber basis weight of each of the plurality of high basis weight portions.

In a second embodiment of the nonwoven fabric as described in the first embodiment of the present invention, the fiber density of each of the plurality of low basis weight portions is less than the fiber density of each of the plurality of high basis weight portions.

In a third embodiment of the nonwoven fabric as described in either the first or second embodiments of the present invention, in the plurality of low basis weight portions the content of fibers oriented in a second direction orthogonal to the first direction is greater than the content of fibers oriented in the first direction.

In a fourth embodiment of the nonwoven fabric as described in any one of the first to third embodiments of the present invention, the plurality of low basis weight portions are respectively a plurality of groove portions recessed in a thickness direction of the nonwoven fabric on a first surface side of the nonwoven fabric, and the plurality of high basis weight portions are a plurality of convex portions projected in the thickness direction on a first surface side.

In a fifth embodiment of the nonwoven fabric as described in the fourth embodiment of the present invention, a fiber basis weight of each of the plurality of groove portions is no greater than 90% of a fiber basis weight of each of the plurality of convex portions.

In a sixth embodiment of the nonwoven fabric as described in either the fourth or fifth embodiments of the present invention, the fiber basis weight of each of the plurality of groove portions is 3 g/m² to 200 g/m², and the basis weight of each of the plurality of convex portions is 15 g/m² to 250 g/m².

In a seventh embodiment of the nonwoven fabric as described in any one of the fourth to sixth embodiments of the present invention, a fiber density of each of the plurality of convex portions is 0.20 g/cm$^3$ or less, and a fiber density of each of the plurality of groove portions is 0.18 g/cm$^3$ or less.

In an eighth embodiment of the nonwoven fabric as described in any one of the fourth to seventh embodiments of the present invention, a height of each of the plurality of groove portions in the thickness direction is no greater than 90% of a height of the convex portion.

In a ninth embodiment of the nonwoven fabric as described in any one of the fourth to eighth embodiments of the present invention, each of the plurality of groove portions has a plurality of areas of fiber basis weights that is less than an average fiber basis weight in a groove bottom.

In a tenth embodiment of nonwoven fabric as described in the ninth embodiment of the present invention, each of the plurality of areas is an opening.

In an eleventh embodiment of the nonwoven fabric as described in the tenth embodiment of the present invention, fibers positioned in a peripheral edge of each of the plurality of openings are oriented along the peripheral edge.

In a twelfth embodiment of the nonwoven fabric as described in any one of the fourth to eleventh embodiments of the present invention, at least one of the plurality of convex portions has a different height in the thickness direction compared to that of the height of the adjoining convex portion sandwiching a groove portion adjacent to the convex portion.

In a thirteenth embodiment of the nonwoven fabric as described in any one of the fourth to twelfth embodiments of the present invention, a top of each of the plurality of convex portions is substantially flat.

In a fourteenth embodiment of the nonwoven fabric as described in any one of the fourth to thirteenth embodiments of the present invention, on a second surface side opposite to the first surface side, a plurality of areas are formed to project to a side opposite to the projecting direction of the plurality of convex portions.

In a fifteenth embodiment of the nonwoven fabric as described in any one of the first to fourteenth embodiments of the present invention, the nonwoven fabric is undulating in the first direction.

In a sixteenth embodiment of the nonwoven fabric as described in any one of the fourth to fourteenth embodiments of the present invention, the second surface side opposite to the first surface side is substantially flat.

In a seventeenth embodiment of the nonwoven fabric as described in any one of the first to sixteenth embodiments of the present invention, fibers constituting the fiber assembly include water-repellant fibers.

According to the present invention, it is possible to provide nonwoven fabric which facilitates permeation of a liquid and at least the basis weight of which, is adjusted.

BRIEF DESCRIPTION OF THE DRAWINGS

FIG. 1 shows a perspective diagram of a fiber web;

FIG. 5 shows a diagram illustrating a state in which a gas is directed to an upper side of the fiber web of FIG. 1, a lower side of which is supported by the net support member of FIG. 4, in order to manufacture the nonwoven fabric of the first embodiment of FIGS. 2A and 2B;

DETAILED DESCRIPTION OF THE INVENTION

Figure 2A:
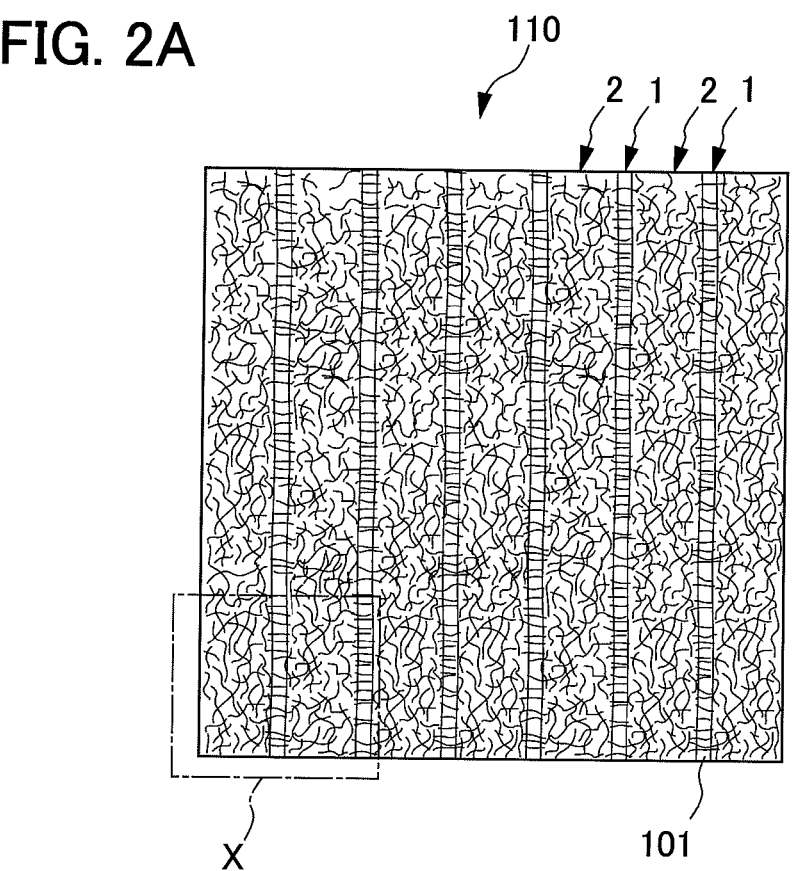
FIGS. 2A and 2B show a plan view and a bottom view of a nonwoven fabric according to a first embodiment.

The preferred embodiments of the present invention will be described with reference to the accompanying figures.

1. FIRST EMBODIMENT

Referring to FIGS. 1 to 5, the nonwoven fabric of first embodiment of the present invention will be described.

The nonwoven fabric 110 of the present embodiment can be manufactured by blowing a fluid, mainly consisting of gas, to a fiber web 100 which is a fiber assembly. The nonwoven fabric includes groove portions 1 which are a plurality of low basis weight portions formed in a longitudinal direction (LD) as a first direction, and convex portions 2 which are a plurality of high basis weight portions formed along the groove portions 1. A fiber basis weight of the groove portion 1 is adjusted to be less than that of the convex portion 2.

1-1. Shape

Figure 2B:
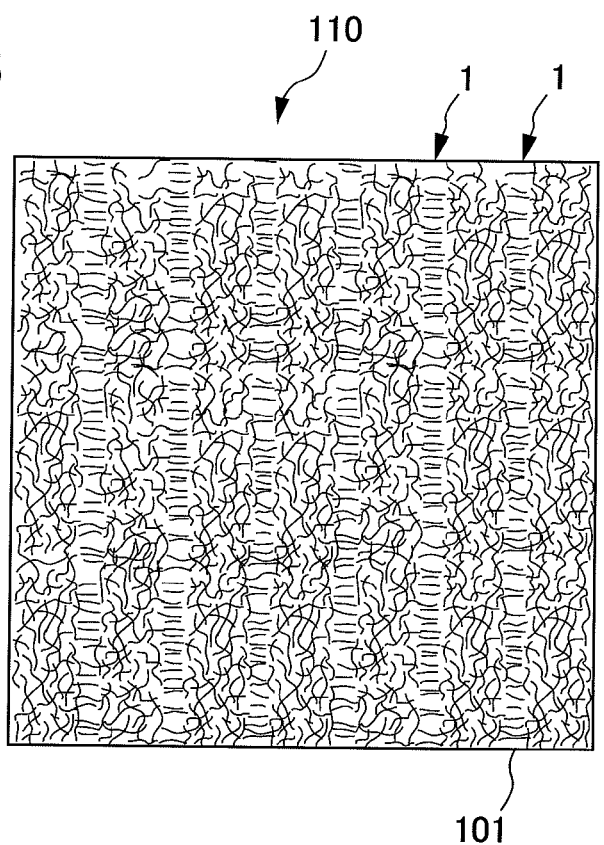
Figure 3:
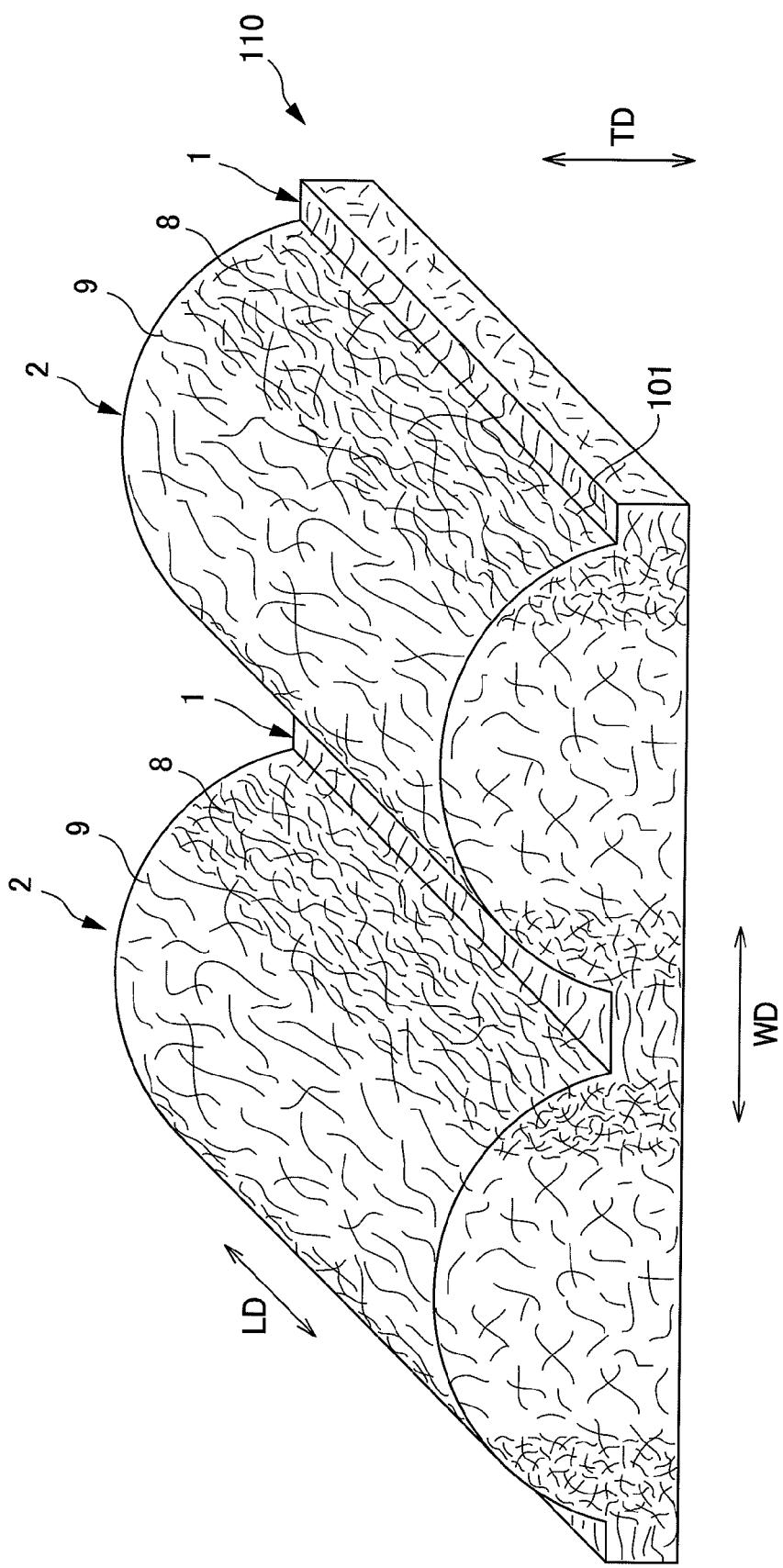
FIG. 3 shows an expanded perspective view of an area X as defined in FIG. 2A.

As shown in FIGS. 2A and 2B and 3, the nonwoven fabric 110 of the present embodiment is a nonwoven fabric in which the plurality of groove portions 1 are formed in parallel at substantially equal spaces on one surface side of the nonwoven fabric 110. The plurality of convex portions 2 are formed among each pair of the plurality of groove portions 1 formed at substantially equal spaces. The convex portions 2 are formed in parallel at substantially equal spaces as in the case of the groove portions 1.

A thickness direction (TD) of the convex portion 2 of the nonwoven fabric 110 of the present embodiment in a thickness direction of the nonwoven fabric 110 is 0.3 to 15 mm, preferably 0.5 to 5 mm. A length of one convex portion 2 in a width direction (WD) is 0.5 to 30 mm, preferably 1.0 to 10 mm. A distance between tops of the convex portions 2 adjacent to each other sandwiching the groove portion 1 is 0.5 to 30 mm, preferably 3 to 10 mm.

A height of the groove portion 1 in a thickness direction (TD) of the nonwoven fabric 110 is no greater than 90% of that of the convex portion 2, preferably 1 to 50%, and more preferably 5 to 20%. A length of the groove portion 1 in a width direction (WD) is 0.1 to 30 mm, preferably 0.5 to 10 mm. A pitch between the groove portions 1 adjacent to each other via the convex portion 2 is 0.5 to 20 mm, preferably 3 to 10 mm.

By this design, in the case of using the nonwoven fabric 110 as a top sheet of an absorbent article for example, even when a large amount of a predetermined liquid is discharged, it is possible to form a groove portion 1 that reduces the likelihood of blotting on the surface caused by the spreading liquid. Even when excessive external pressure is applied to the nonwoven fabric 110 to crush the convex portion 2, the integrity of the space of the groove portion 1 is maintained. Even in the event when an external pressure is applied to the nonwoven fabric 110 and a predetermined liquid is discharged, it is possible to suppress wide blotting of the surface with the liquid. Furthermore, even when a predetermined liquid absorbed by an absorbent is leached as a result of external pressure, because of the concaves and convexes formed in the surface of the nonwoven fabric 110, contact area with the skin is reduced. Thus, it may be difficult for the liquid to widely adhere to the skin.

A method for measuring a height, a pitch and a width of the groove portion 1 or the convex portion 2 is described as follows. For example, the nonwoven fabric 110 is set on a table in the absence external pressurized, and the height, the pitch and the width are measured from a sectional photograph or video footage of the nonwoven fabric taken by a microscope. The nonwoven fabric 110 as a sample is cut crossing the convex portion 2 and the groove portion 1.

A height (length in the thickness direction (TD)) is measured by setting a highest position of each of the convex portion 2 and the groove portion 1 formed in a direction from a lowest position (table surface) of the nonwoven fabric 110 upward as a height.

To measure a pitch between the adjacent convex portions 2, a distance between tops of the adjacent convex portions 2 is measured. To measure a pitch between the adjacent groove portions 1, similarly, a distance from a center of the groove portion 1 in a width direction (WD) to a center of the adjacent groove portion 1 in the width direction (WD) is measured.

To measure a width, a maximum width of a bottom surface of the convex portion 2 directed from the lowest position (table surface) of the nonwoven fabric 110 upward is measured, and a maximum width of a bottom surface of the groove portion 1 is similarly measured.

There is no limitation on a sectional shape of the convex portion 2. For example, a dome shape, a trapezoidal shape, a triangular shape, an Ω-shape, a square shape or the like can be used. To improve the positive feelings when in contact with the skin, the vicinity of the top surface or the side face of the convex portion 2 should preferably be curved. To maintain the space by the groove portion 1 without crushing the convex portion 2 when external pressure is applied, the width should preferably be narrower from the bottom surface to the top of the convex portion 2. A preferable shape of the convex portion 2 is a curved-line (curved-surface) shape such as a substantially dome shape.

According to the present embodiment, the groove portions 1 are formed in parallel at substantially equal spaces. However, this formation is in no way limiting. For example, groove portions may be formed at different spaces, or formed so that a space can be changed between adjacent groove portions 1.

According to the present embodiment, heights of (thickness direction TD) of the convex portions 2 of the nonwoven fabric 110 are substantially uniform. However, for example, adjacent convex portions 2 may be formed to be different from each other in height. By adjusting a space between blowing nozzles 913 through which a fluid, mainly consisting of gas, is discharged, the height of the convex portion 2 can be adjusted. For example, the height of the convex portion 2 can be reduced by narrowing the space between the blowing nozzles 913. The height of the convex portion 2 can be increased by widening the space between the blowing nozzles 913. Additionally, convex portions 2 differing in height can be alternately formed by alternating narrow and wide spaces among the blowing nozzles 913. Partially changing the height of the convex portion 2 is advantageous in that damage on the skin can be reduced as the contact area with the skin is less.

1-2. Fiber Orientation

As shown in FIGS. 2A and 2B and 3, in the nonwoven fabric 110, areas different in contents of longitudinally-oriented fibers in which fibers 101 are oriented in a longitudinal direction (LD) as a first direction are formed. Examples include a side potion 8 and a central portion 9 constituting the groove portion 1 and the convex portion 2. The longitudinal direction (LD) is a direction in which a fiber web is delivered via a nonwoven fabric manufacturing apparatus.

The orientation of the fiber 101 in the longitudinal direction (LD) means that the fiber 101 is oriented within a range of +45° to −45° in the longitudinal direction, and a fiber oriented in the longitudinal direction (LD) is regarded as a longitudinally-oriented fiber. Orientation of the fiber 101 in the width direction (WD) means that the fiber 101 is oriented within a range of +45° to −45° in the width direction (WD) orthogonal to the longitudinal direction (LD), and a fiber oriented in the width direction (WD) is regarded as a laterally-oriented fiber.

The side potions 8 are areas equivalent to both sides of the convex portion 2, and the fibers 101 of the side potion 8 are formed so that a content of longitudinally-oriented fibers is greater than that of longitudinally-oriented fibers of the central potion 9 (area sandwiched by the side potions 8 in the convex portion 2). For example, a content of longitudinally-oriented fibers in the side potion 8 is 55 to 100%, preferably 60 to 100%. If the content of longitudinally-oriented fibers in the side potion 8 is less than 55%, the side potion 8 may elongate as a result of line tension. If the side potion 8 becomes elongated, the groove portion 1 or the central potion 9 described below may also become elongated as a result of line tension.

The central potion 9 is an area sandwiched by the side potions 8 equivalent to both sides of the convex portion 2, in which a content of longitudinally-oriented fibers is less than that of the side potion 8. It is preferable that the longitudinally-oriented fibers and laterally-oriented fibers are moderately mixed in the central portions 9.

For example, the central potion 9 is formed so that the content of longitudinally-oriented fibers is 10% less than that of longitudinally-oriented fibers of the side potion 8, and 10% greater than that of longitudinally-oriented fibers in the bottom of the groove portion 1 described below. Specifically, the content of longitudinally-oriented fibers of the central potion 9 should preferably be within a range of 40 to 80%.

As the groove portion 1 are regions onto which a fluid, mainly consisting of gas (e.g., hot air), is directed, the longitudinally-oriented fibers of the groove portion 1 are collected on the side potion 8. Then, the laterally-oriented fibers of the groove portion 1 are left in the bottom thereof. Accordingly, in the fibers 101 of the bottom of the groove portion 1, a content of laterally-oriented fibers is greater than that of longitudinally-oriented fibers.

For example, the content of longitudinally-oriented fibers of the groove portion 1 is at least 10% less than that of longitudinally-oriented fibers of the central potion 9. Thus, in the bottom of the groove portion 1, in the nonwoven fabric 110, the content of longitudinally-oriented fibers is the least while the content of the laterally-oriented fibers is the greatest. Specifically, the content of laterally-oriented fibers is 55 to 100%, preferably 60 to 100%. If the content of laterally-oriented fibers is less than 55%, it is difficult to increase the strength of the nonwoven fabric in the width direction (WD) as the fiber basis weight of the groove portion 1 is low as described below. Then, for example, when the nonwoven fabric 110 is used as a top sheet of an absorbent article, there is the risk that friction, arising from contact with the body of the user, may cause kinking or breakage in the width direction (WD) during use of the absorbent article.

Measurement of fiber orientation was carried out as follows by using a digital microscope VHX-100 made by Keyence Corporation. (1) A sample is set on an observation base so that a longitudinal direction (LD) can be a longitudinal direction, (2) fibers irregularly protruding from the front of the sample are except to set the focus of a lens on the closest fiber, and (3) a photographing depth (depth) is set to create a 3D image of the sample on a computer screen. (4) The 3D image is converted into a 2D image, and (5) a plurality of parallel lines to equally divide the longitudinal direction (LD) within a measuring range are drawn on the screen. (6) In each cell subdivided by drawing the parallel lines, fiber orientation, whether in a longitudinal direction (LD) or a width direction (WD), is observed, and the number of fibers oriented in each direction is measured. (7) Ratio of the number of fibers oriented in the longitudinal direction (LD) and the number of fibers oriented in the width direction (WD) are calculated with respect to the total number of fibers within a set range. Accordingly, measurement and calculation can be carried out.

1-3. Fiber Density

As shown in FIG. 3, the groove portion 1 is adjusted so that a fiber density of the fibers 101 is less than that of the convex portion 2. The fiber density of the groove portion 1 can be freely adjusted according to conditions such as the amount of a fluid (e.g., hot air), mainly consisting of gas, and tension. Fiber density of the convex portion 2 is formed to be greater than that of the groove portion.

A fiber density of the bottom of the groove portion 1 is specifically 0.002 to 1.18 $g/cm^3$ or 0.005 to 0.05 $g/cm^3$. If the fiber density of the bottom of the groove portion 1 is less than 0.002 $g/cm^3$, for example, when the nonwoven fabric 110 is used as an absorbent article, the nonwoven fabric 110 may be easily damaged. If the fiber density of the bottom of the groove portion 1 is greater than 0.18 $g/cm^3$, downward movement of a liquid becomes difficult. Thus, there is the possibility that the liquid will stay in the bottom of the groove portion 1 and impart a wet feeling to the user.

The fiber density of the convex portion 2 is adjusted to be greater than that of the groove portion 1. Specifically, the fiber density is 0.005 to 0.20 $g/cm^3$, more preferably 0.007 to 0.07 $g/cm^3$. If a fiber density of the convex portion 2 is less than 0.005 $g/cm^3$, not only is the convex portion 2 is easily crushed by an own weight of a liquid contained in the convex portion 2 or external pressure but also the absorbed liquid is easily leached under pressure. If the fiber density of the convex portion 2 is greater than 0.20 $g/cm^3$, downward movement of a predetermined liquid collected in the convex portion 2 becomes difficult. Thus, the liquid may remain in the convex portion and impart a wet feeling to the user.

1-4. Fiber Basis Weight

An entire fiber basis weight of the nonwoven fabric 110 is specifically 10 to 200 $g/m^2$, preferably 20 to 100 $g/m^2$. For example, when the nonwoven fabric 110 is used as a top sheet of an absorbent article, if a fiber basis weight is less than 10 $g/m^2$, the nonwoven fabric 110 may be damaged during use. If a fiber basis weight of the nonwoven fabric 110 is greater than 200 $g/m^2$, smooth downward movement of the discharged liquid may be difficult.

As shown in FIGS. 2A and 2B and 3, the fiber basis weight of the bottom of the groove portion 1 is adjusted so that a fiber basis weight of the fibers 101 is less than that of the convex portion 2. The fiber basis weight in the bottom of the groove portion 1 is adjusted to be less than an average fiber basis weight of all the fibers including those of the groove portion 1 and the convex portion 2.

Specifically, a fiber basis weight in the bottom of the groove portion 1 is 3 to 150 $g/m^2$, preferably 5 to 80 $g/m^2$. If the fiber basis weight of the bottom of the groove portion 1 is less than 3 $g/m^2$, when the nonwoven fabric is used, for example, as a top sheet of an absorbent article, the top sheet may easily be damaged during use of the absorbent article. If the fiber basis weight of the bottom of the groove portion 1 is greater than 150 $g/m^2$, downward movement of the liquid brought to the groove portion 1 becomes difficult. Thus, there is the possibility that the liquid will remain in the groove portion 1 and impart a wet feeling to the user.

The convex portion 2 is adjusted so that an average fiber basis weight of the fiber 101 is greater than that of the groove portion 1. For example, a fiber basis weight of the central potion 9 of the convex portion 2 is 15 to 250 $g/m^2$, preferably 20 to 120 $g/m^2$. If a fiber basis weight of the central potion 9 is less than 15 $g/m^2$, not only is the convex portion 2 is easily crushed by the weight of a liquid contained in the central potion 9 or external pressure, but also absorbed liquid is easily leached. If the fiber basis weight of the central portion 9 is greater than 250 $g/m^2$, downward movement of the liquid brought in becomes difficult. Thus, the liquid may stay in the central portion 9 and impart a wet feeling to the user.

A fiber basis weight of the side potion 8 as a side of the convex portion 2 can be freely adjusted according to various conditions including the amount of a liquid (e.g., hot air), mainly consisting of gas, and tension applied to the nonwoven fabric 110. Specifically, the fiber basis weight of the side potion 8 is 20 to 280 $g/m^2$, preferably 25 to 150 $g/m^2$. If the fiber basis weight of the side potion 8 is less than 20 $g/m^2$, the side potion 8 may be elongated by line tension applied during manufacturing of the nonwoven fabric 110. If the fiber basis weight of the side potion 8 is greater than 280 $g/m^2$, during use of the nonwoven fabric 110, downward movement of a liquid brought to the side potion 8 becomes difficult. Thus, there is a possibility that the liquid will stay in the side potion 8 and impart a wet feeling to the user.

1-5. Others

For example, when the nonwoven fabric of the present embodiment is used for absorbing or transmitting a predetermined liquid, the groove portion 1 transfers the liquid while it is difficult to hold the liquid in the convex portion 2 because of its porous structure.

The bottom of the groove portion 1 is suited to permeation of liquid as the fiber density of the fibers 101 is low and the fiber basis weight is low. As the fibers 101 of the bottom of the groove portion 1 are oriented in the width direction (WD), it is possible to prevent wide spreading of the liquid excessively flown in the longitudinal direction (LD) of the groove portion 1. As the fibers 101 are oriented in the width direction (WD) of the groove portion 1 while its basis weight is low, the strength of the nonwoven fabric in the width direction (WD) is higher.

The fiber basis weight of the convex portion 2 is adjusted to be high. Accordingly, the number of fibers in the convex portion 2 increases to increase the number of thermally bonded points, thereby maintaining a porous structure.

The groove portion 1 has a content of laterally-oriented fibers per unit area which is greater than that of the central portion 9, and the side potion 2 has a content of longitudinally-oriented fibers per unit area which is greater higher than that of the central portion 9. The central portion 9 includes a larger number of fibers 101 oriented in the thickness direction (TD) compared to that of the groove portion 1 and the side potion 8. Thus, for example, even if a load in the thickness direction (TD) is applied to the central portion 9 and reduces the thickness of the convex portion 2, when the load is released, the original height is easily restored to the stiffness of the fibers 101 oriented in the thickness direction (TD). In other words, the nonwoven fabric 110 is a nonwoven fabric of high compression restoration.

1-6. Manufacturing Method

Referring to FIGS. 4A to 9, a method for manufacturing the nonwoven fabric 110 of the present embodiment will be described. A fiber web 100 is set on an upper surface side of a net support member 210 which is an air permeable support member shown in FIGS. 4A and 4B. In other words, the fiber web 100 is supported from the lower side by the net support member 210.

As shown in FIG. 5, the net support member 210 in the state of supporting the fiber web 100 is moved in a predetermined direction, and a gas is continuously blown from the upper surface side of the moving fiber web 100, whereby the nonwoven fabric 110 of the present embodiment can be manufactured.

The net support member 210 is formed by interweaving a plurality of wires 211 of predetermined thicknesses which are not air permeable portions. By interweaving the plurality of wires 211 at predetermined spaces, a net support member 210 which includes a plurality of holes 213 as air permeable portions is obtained.

Figure 4A:
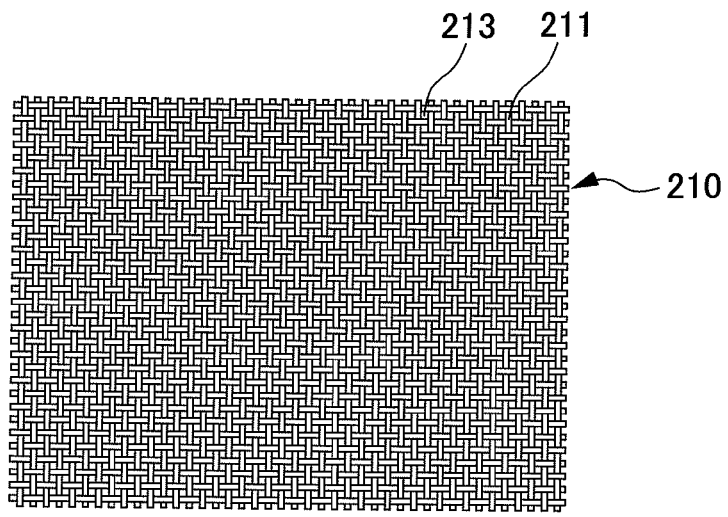
FIGS. 4A and 4B show a plan view and a perspective view of a net support member.
Figure 4B:
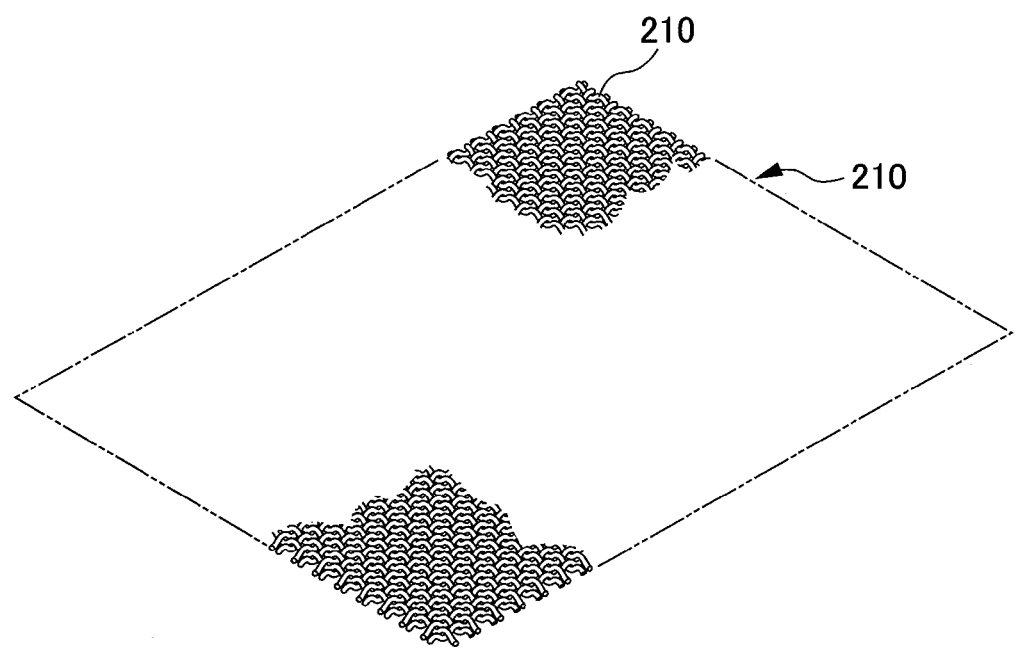

As shown in FIGS. 4A and 4B, the net support member 210 includes a plurality of small-diameter holes 213, and the gas directed from the upper surface side of the fiber web 100 is vented downward without being blocked by the net support member 210. The net support member 210 does not largely change the flow of fluid, mainly containing gas to be directed thereupon, and the fibers 101 are not moved in a lower direction of the net support member 210.

Accordingly, the fibers 101 of the fiber web 100 are moved in a predetermined direction mainly by the fluid mainly containing gas to be directed from the upper surface side. Specifically, as downward movement of the net support member 210 is regulated, the fibers 101 are moved along a surface of the net support member 210.

For example, the fibers 101 of an area to which the fluid mainly consisting gas is directed are moved to an area adjacent to the area. The area to which the fluid mainly consisting gas is directed is relatively moved in a predetermined direction. As a result, the fibers are moved to areas on the side of the areas continuous in the fluid mainly consisting gas blowing direction.

Thus, the groove portion 1 is formed, and those of the fibers 101 of the bottom of the groove portion 1 oriented in the width direction remain. A convex portion 2 is formed between the groove portions 1, a fiber density of the side of the convex portion 2 is high, and the fibers 101 are oriented in the longitudinal direction (LD).

Figure 6:
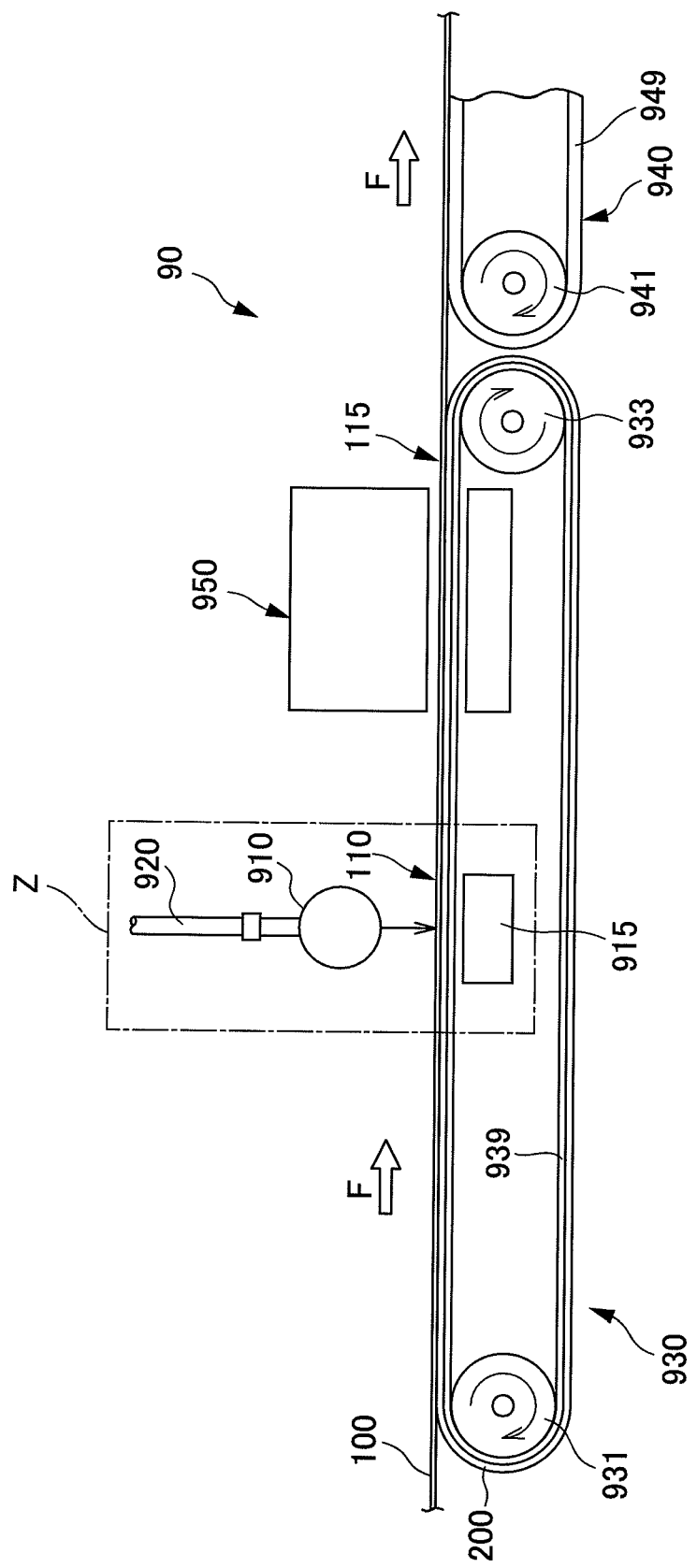
FIG. 6 shows a side view illustrating a nonwoven fabric manufacturing apparatus according to the first embodiment.
Figure 7:
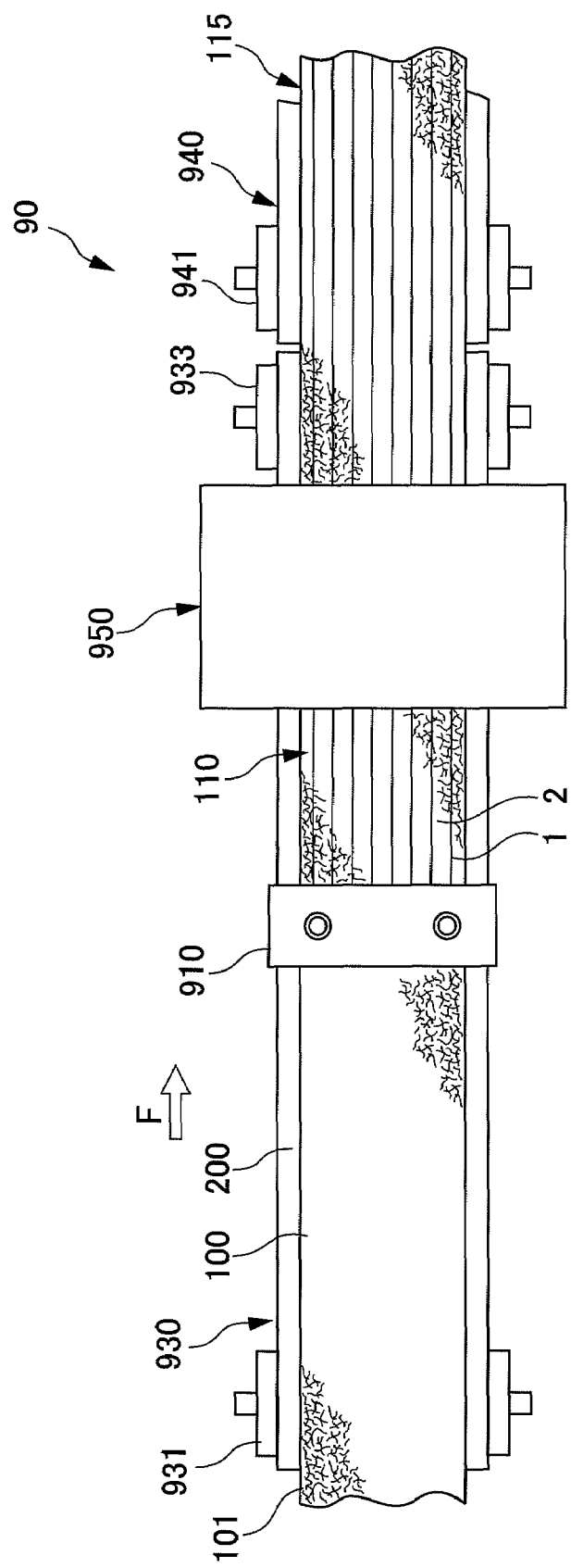
FIG. 7 shows a plan view illustrating the nonwoven fabric manufacturing apparatus of FIG. 6.

As shown in FIGS. 6 and 7, an nonwoven fabric manufacturing apparatus 90 for manufacturing the nonwoven fabric 110 of the embodiment includes an air-permeable support member 200 for supporting the fiber web 100 as a fiber assembly from one surface side, a blowing unit 910 as a blowing means for blowing a fluid, mainly consisting of gas, to the fiber web 100 as the fiber assembly supported by one surface side of the air-permeable support member 200 from the other surface side in the fiber web 100 as the fiber assembly, and an air supply portion (not shown).

In the nonwoven fabric manufacturing apparatus 90, the nonwoven fabric 110 is formed by sequentially moving the fiber web 100 by moving means. The moving means moves the fiber web 100 as the fiber assembly in the state of being supported from one surface side by the air-permeable support member 200 in a predetermined direction. Specifically, the fiber web 100 in the directed state of the gas, mainly consisting of gas, is moved in a predetermined direction F. An example of the moving means is a conveyor 930 shown in FIG. 6. The conveyor 930 constituted with an air permeable belt 939 on which is formed in a laterally elongated ring shape to mount the air-permeable support member 200, and rotation potions 931 and 933 are arranged at both ends of the longitudinal direction (LD) inside the air permeable belt 939 formed in the laterally elongated ring shape to rotate the ring-shaped air permeable belt 939 in a predetermined direction.

The air-permeable support member 200 can be replaced as occasion demands depending on nonwoven fabric to be manufactured. For example, in the case of manufacturing the nonwoven fabric 110 of the present embodiment, the net support member 210 can be used as the air-permeable support member 200.

As described above, the conveyor 930 moves the air-permeable support member 200 (net support member 210) in the state of supporting the fiber web 100 from the lower surface side in the predetermined direction F. Specifically, as shown in FIG. 6, the air-permeable support member 200 moves the fiber web 100 through the lower side of the blowing unit 910. Additionally, the air-permeable support member 200 moves the fiber web 100 into a heater 950 as a heating means opened in both sides.

Figure 9:
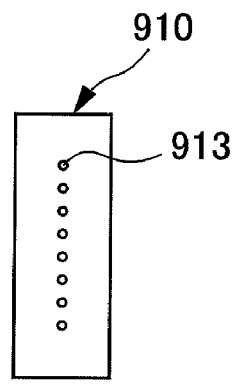
FIG. 9 shows a bottom view of a blowing unit of FIG. 8.

The directing means includes an air supply portion (not shown) and a blowing unit 910. The air supply unit (not shown) is connected to the blowing unit 910 via an air supply pipe 920. The air supply pipe 920 is connected to the upper side of the blowing unit 910 to communicate. As shown in FIG. 9, the blowing unit 910 includes a plurality of blowing nozzles 913 at predetermined spaces.

Figure 8:
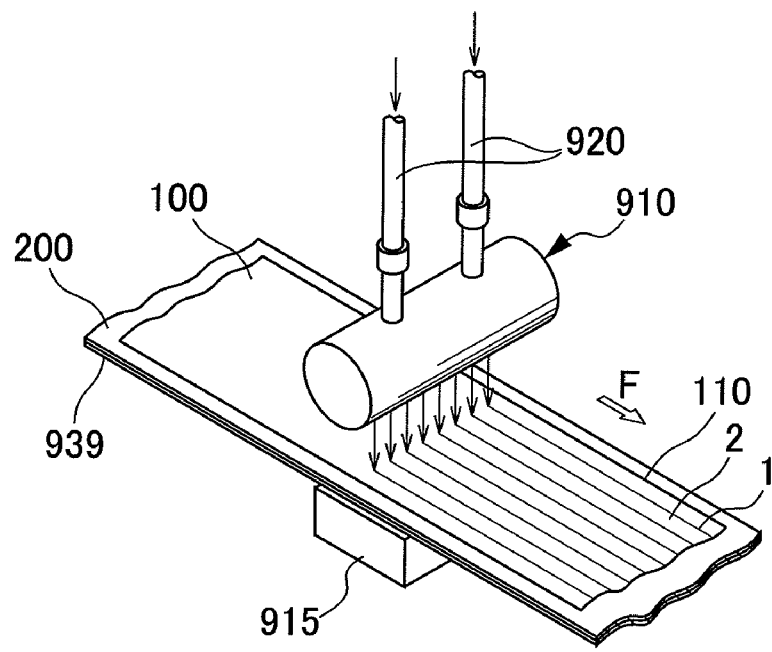
FIG. 8 shows an expanded perspective view of an area Z as defined in FIG. 6.

As shown in FIG. 8, a gas supplied from the air supplying unit (not shown) through the air supply pipe 920 to the blowing unit 910 is directed from the plurality of blowing nozzles 913 formed in the blowing unit 910. The gas ejected from the plurality of blowing nozzles 913 is continuously directed to the upper surface side of the fiber web 100 supported from the lower surface side by the air-permeable support member 200 (net support member 210). Specifically, the gas from the plurality of blowing nozzles 913 is continuously directed to the upper surface side of the fiber web 100 in the state of being moved in the predetermined direction F by the conveyor 930.

An suction unit 915 arranged in the lower side of the air-permeable support member 200 (net support member 210) below the blowing unit 910 sucks the gas being directed from the blowing unit 910 to ventilate the air-permeable support member 200 (net support member 210). The suction of the suction portion 915 also enables positioning of the fiber web 100 to adhere to the air-permeable support member 200 (net support member 210).

The suction of the suction unit 915 only needs to be a level which enables pressing the fibers 101 of the area receiving the fluid, mainly consisting of gas, to the air-permeable support member 200 (net support member 210). The suction unit 915 sucks (suction) the directed fluid, mainly consisting of gas, whereby the fluid, mainly consisting of gas, applied to a non air permeable portion (e.g., wire 211 of the net support member 210) of the air-permeable support member 200 is prevented from bouncing to disturb the shape of the fiber web 100. The fiber web can be conveyed into the heater 950 while the shape of the groove portion (concave and convex portion) formed by the air flow is maintained. In this case, the fiber web should preferably be conveyed into the heater 950 by sucking simultaneously with the formation by the air flow while suction is being performed.

By sucking the fluid mainly consisting of gas, from the lower side of the air-permeable support member 200 (net support member 210), the fibers of the area to which the fluid mainly consisting of gas, being directed are moved while being pressed to the air-permeable support member 200 (net support member 210). Accordingly, the fibers gather on the air-permeable support member 200 (net support member 210) side. In the convex portion 2, the directed fluid, mainly consisting of gas, clashes with the non air permeable portion (e.g., wire 211 of the net support member 210) of the air-permeable support member 200 to be bounced, and thus the fibers 101 are partially set in the thickness direction (TD).

The temperature of the fluid, mainly consisting of gas, directed from the blowing nozzles 913 may be a normal temperature as described above. However, for example, in the case of improving the ability to mold the groove portion (concave and convex portion), the temperature can be adjusted to a temperature at least equal to or greater than a softening point of thermoplastic fibers constituting the fiber assembly, preferably a temperature equal to or more than the softening point and +50° C. to −50° C. of the melting point of the fiber. When the fibers are softened, bouncing forces of the fibers themselves are lowered. Thus, the rearranged shape of the fibers by the air flow is easily maintained. When the temperature is further increased, thermal bonding of the fibers commences, thereby facilitating the maintenance of the shape of the groove portion (concave and convex portion). As a result, the fiber web can easily be conveyed into the heater 950 in the state of maintaining the shape of the groove portion (concave and convex portion).

The shape of the convex portion 2 can be changed by adjusting an amount, a temperature, or a suction amount of the fluid, mainly consisting of gas, to be directed, air fiber basis weight of the fiber web 100. For example, if the and the amount of a fluid, mainly consisting of gas, to be sucked (suction) are almost equal, or the amount of a fluid, mainly consisting of gas, to be sucked is greater than that of the fluid, mainly consisting of gas, to be directed, a backside of the convex portion 2 of nonwoven fabric 115 (nonwoven fabric 110) is formed to match the shape of the air-permeable support member 200 (net support member 210). Accordingly, when the air-permeable support member 200 (net support member 210) is flat, the backside of the nonwoven fabric 115 (nonwoven fabric 110) is substantially flat.

To convey the fiber web 100 into the heater 950 in the state of firmly maintaining the shape of the groove portion (concave and convex portion) formed by the air flow, the fiber web 100 is conveyed into the heater 950 immediately after the groove portion (concave and convex portion) is formed in the fiber web 100 by an air flow or simultaneously with the formation of the groove portion (concave and convex portion), or cooled by cold air immediately after the groove portion (concave and convex portion) is formed in the fiber web 100 by hot air (air flow of a predetermined temperature). Then, the fiber web 100 can be conveyed into the heater 950.

The heater 950 as a heating means has both ends open in the predetermined direction F. Accordingly, the fiber web 100 set on the air-permeable support member 200 (net support member 210) moved by the conveyor 930 is continuously moved after staying in a heated space formed in the heater 950 for a predetermined time. For example, when the fibers 101 constituting the fiber web 100 (nonwoven fabric 110) include thermoplastic fibers, the nonwoven fabric 115 (nonwoven fabric 110) in which fibers 101 are bonded by heating of the heater 950 can be obtained.

2. OTHER EMBODIMENTS

Nonwoven fabric of the other embodiments of the present invention will be described below. In the description of the embodiments below, portions not described are similar to those of the nonwoven fabric of the first embodiment, and numbers in the drawings are identical when portions are similar to those of the first embodiment.

Referring to FIGS. 10 to 16, nonwoven fabric of the second to sixth embodiments of the present invention will be described. According to the second embodiment, a shape of the nonwoven fabric is different. According to the third embodiment, a shape of the entire nonwoven fabric is different. According to the fourth embodiment, a surface opposed to a surface in which the groove portion and the convex portion area formed is different in the nonwoven fabric. According to the fifth embodiment, a convex portion of the nonwoven fabric is different. The sixth embodiment is another embodiment regarding an opening of the nonwoven fabric.

2-1. SECOND EMBODIMENT

Figure 10:
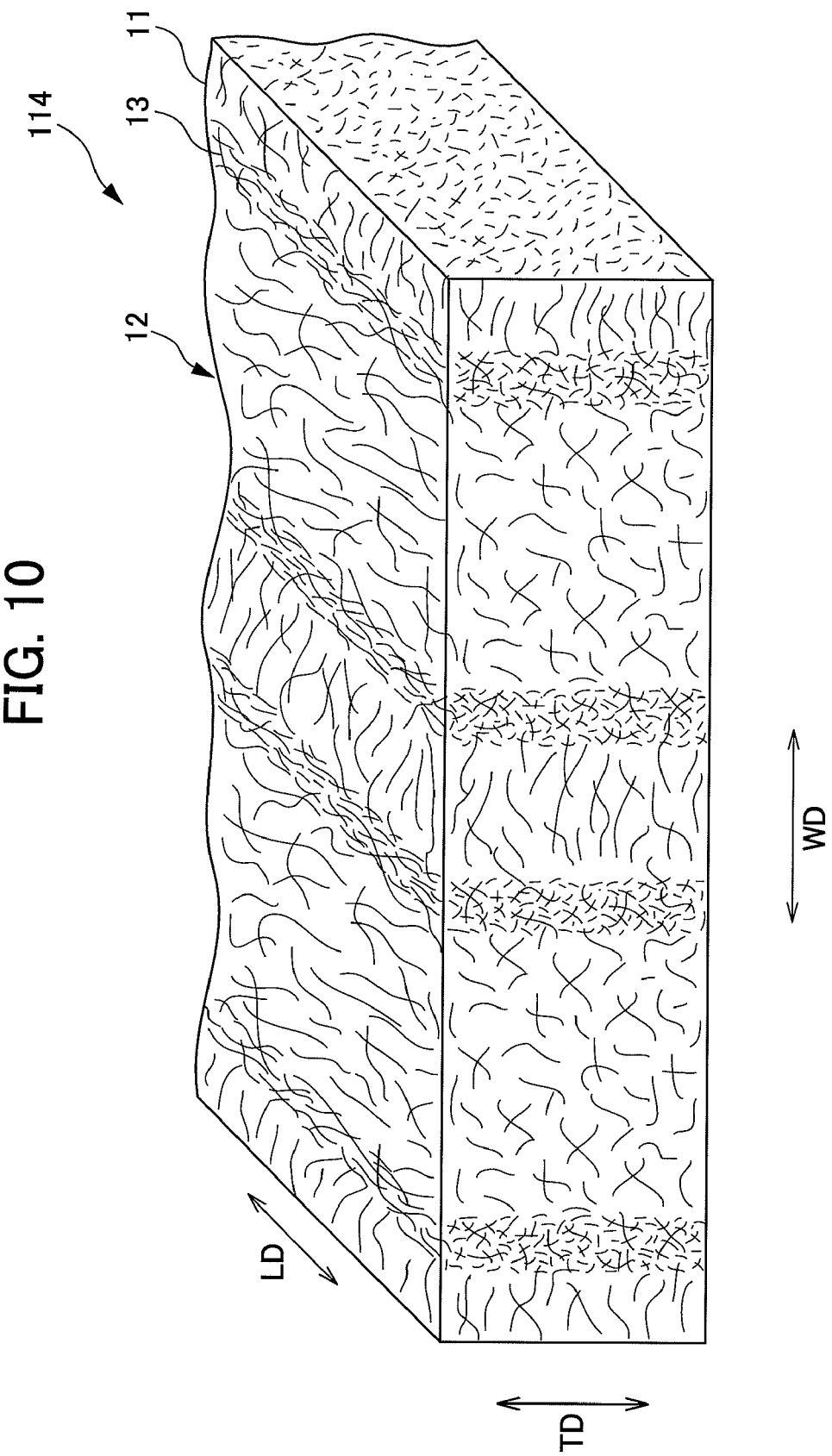
FIG. 10 shows an expanded perspective view of a nonwoven fabric according to a second embodiment.

Referring to FIG. 10, the nonwoven fabric of the second embodiment of the present invention will be described.

2-1-1. Overview

As shown in FIG. 10, nonwoven fabric 114 of the present embodiment has both surfaces substantially flat. This nonwoven fabric includes areas varied in fiber orientation or the like in a predetermined area. Points different from the first embodiment will be mainly described below.

2.1.2 Fiber Orientation

As shown in FIG. 10, in the nonwoven fabric 114, a plurality of areas with differing contents of longitudinally-oriented fibers are formed. Examples of the plurality of areas differing in content of longitudinally-oriented fibers are a longitudinally oriented portion 13 which is a second area having the highest content of longitudinally-oriented fibers, a center portion 12 which is a third area having a content of longitudinally-oriented fibers that is lower than that of the longitudinally oriented portion 13, and a laterally oriented portion 11 which is a first area having the lowest content of longitudinally-oriented fibers and the highest content of laterally-oriented fibers. In the nonwoven fabric 114, a plurality of longitudinally oriented portions 13 are formed along both sides of a plurality of laterally oriented portions 11. A plurality of center portions 12 are positioned on a side opposed to the side of the laterally oriented portions 11 in the plurality of longitudinally oriented portions 13, and formed in areas sandwiched by the adjacent longitudinally oriented portions 13.

The laterally oriented portion 11 is an area constituted of remaining fibers 101 after fibers 101 oriented in a longitudinal direction (LD) which is a longitudinal direction in a fiber web 100 are collected on the longitudinally oriented portion 13 side by a fluid, mainly consisting of gas. In other words, as the fibers 101 directed in the longitudinal direction (LD) are moved to the longitudinally oriented portion 13 side by the fluid, mainly consisting of gas, in the laterally oriented portion 11, laterally-oriented fibers oriented in a width direction (WD) which is a horizontal direction are mainly left in the fiber web 100. Accordingly, most of the fibers 101 of the laterally oriented portion 11 are oriented in the orthogonal direction (width direction (WD)) with respect to the longitudinal direction (LD). A fiber basis weight of the laterally oriented portion 11 is adjusted to be low as described below. However, as most of the fibers 101 of the laterally oriented portion 11 are oriented in the width direction (WD), tensile strength is high in the width direction (WD). Thus, for example, when the nonwoven fabric 114 is used as a top sheet of an absorbent article, it is possible to prevent damage even if force of friction is applied in the width direction (WD) during use.

The longitudinally oriented portion 13 is formed by blowing a fluid, mainly consisting of gas, to the fibers 101 directed in the longitudinal direction (LD) of the fiber web 100 to bring the same to the longitudinally oriented portion 13 side. As many of the fibers 101 of the longitudinally oriented portion 13 are oriented in the longitudinal direction LD), the inter fiber distance of the fibers 101 is short, and the fiber density is high. As a result, stiffness is increased.

2-1-3. Fiber Density

As shown in FIG. 10, blowing of the fluid, mainly consisting of gas, moves the fibers 101 of the laterally oriented portion 11 and, by pressure of the directed fluid, mainly consisting of gas, the fibers 101 move and gather on a lower side of the nonwoven fabric 114 in a thickness direction (TD). Accordingly, space area rates are respectively high and low in the upper and lower sides of the nonwoven fabric 114 in the thickness direction (TD). In other words, fiber densities are respectively low and high in the upper and lower sides of the nonwoven fabric 114 in the thickness direction (TD).

The laterally oriented portion 11 is formed such that the blowing of the fluid, mainly consisting of gas, causes movement of the fibers 101 to reduce a fiber density. On the other hand, as the longitudinally oriented portion 13 is an area in which the fibers 101 moved from the laterally oriented portion 11 gather, it is formed such that its fiber density is greater than that of the laterally oriented portion 11. A center 12 is formed such that its fiber density is in between those of the horizontally and longitudinally oriented portions 11 and 13.

2-1-4. Fiber Basis Weight

As shown in FIG. 10, as the fibers 101 move to the other area by the fluid, mainly consisting of gas, directed to the laterally oriented portion 11, a fiber basis weight of the laterally oriented portion 11 is lowest. As the fibers 101 moved from the laterally oriented portion 11 are collected by the fluid, mainly consisting of gas, a fiber basis weight of the longitudinally oriented portion 13 is highest. Then, a center portion 12 is formed in a manner that both sides are held between the longitudinally oriented portions 13. In other words, the center or the laterally oriented portion 11 which is an area of a low fiber basis weight is formed such that the longitudinally oriented portions 13 are supported on both sides. Thus, for example, it is possible to suppress elongation by line tension during manufacturing of the nonwoven fabric 114 even if a fiber basis weight is low.

2-1-5. Others

For example, when the nonwoven fabric 114 is used for a top sheet of an absorbent article, the nonwoven fabric 114 can be used while the laterally oriented portion 11 or the center portion 12 of a low fiber basis weight is maintained, in other words, in an un-elongated state by line tension during product manufacturing. As the longitudinally oriented portion 13 of a high fiber basis weight is formed between the laterally oriented portion 11 and the center, when a liquid is absorbed, crushing of the nonwoven fabric 114 by the weight of the liquid or by its own weight is difficult. As a result, even when liquids are repeatedly discharged, it is possible to move the liquids to the lower side of the nonwoven fabric 114 without spreading the liquids on the surface.

2-1-6. Manufacturing Method

A method for manufacturing the nonwoven fabric 114 of the present embodiment will be described below. First, the fiber web 100 is set on the upper surface side of the net support member 210 which is an air-permeable support member 200. In other words, the fiber web 100 is supported from the lower side by the net support member 210. For this net support member 210, the same as the net support member 210 of the first embodiment can be used.

Then, the net support member 210 in the state of supporting the fiber web 100 is moved in a predetermined direction, and a fluid, mainly consisting of gas, is continuously directed from an upper surface side of the moved fiber web 100, whereby the nonwoven fabric 114 of the present embodiment can be manufactured.

The amount of a fluid, mainly consisting of gas, directed to the nonwoven fabric 114 only needs to be at a level that allows movement of fibers 101 of the fiber web 100 in an area to which the fluid, mainly consisting of gas, is directed can be moved in a width direction (WD). In this case, preferably, the spayed fluid, mainly consisting of gas, is not sucked by a suction portion 915 for sucking the fluid to the lower side of the net support member 210. However, the fluid may be sucked by an amount in which the laterally oriented portion 11 is not pressed by the net support member 210.

For example, nonwoven fabric having a concave and convex portion such as a groove portion or a convex portion may be formed by directed the fluid mainly consisting of gas, and then the formed concave and convex portion may be crushed by winding the nonwoven fabric on a roll.

Thus, by reducing a force of pressing the fibers 101 to the lower side, it is possible to form nonwoven fabric 114 of a substantially uniform thickness without forming any concave and convex portions.

The nonwoven fabric 114 of the present embodiment can be manufactured by a nonwoven fabric manufacturing apparatus 90. For a manufacturing method of the nonwoven fabric in the nonwoven fabric manufacturing apparatus 90, the description of the manufacturing method of the nonwoven fabric and the nonwoven fabric manufacturing apparatus 90 of the first embodiment can be referred to.

2-2 THIRD EMBODIMENT

Figure 11:
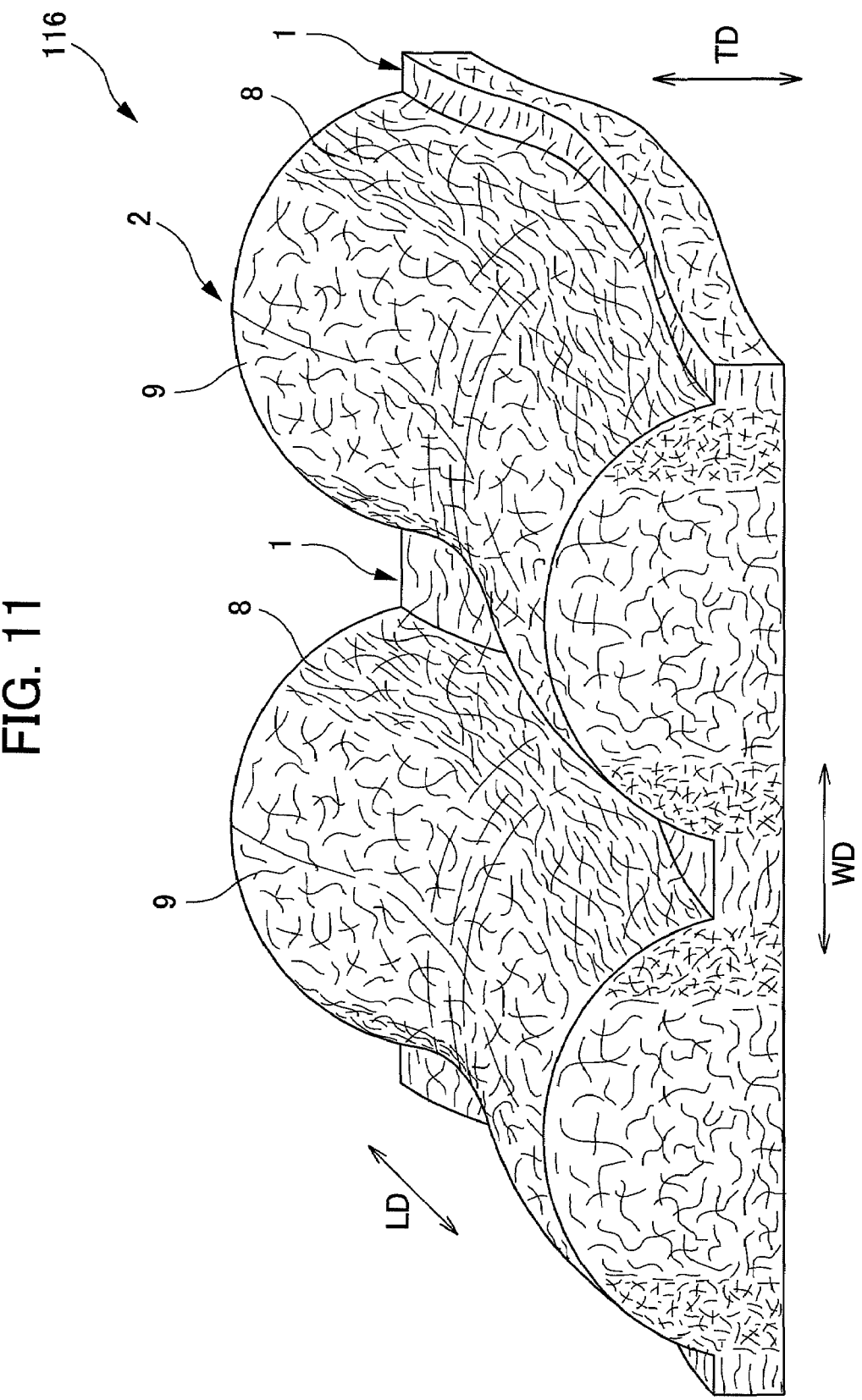
FIG. 11 shows an expanded perspective view of a nonwoven fabric according to a third embodiment.
Figure 12:
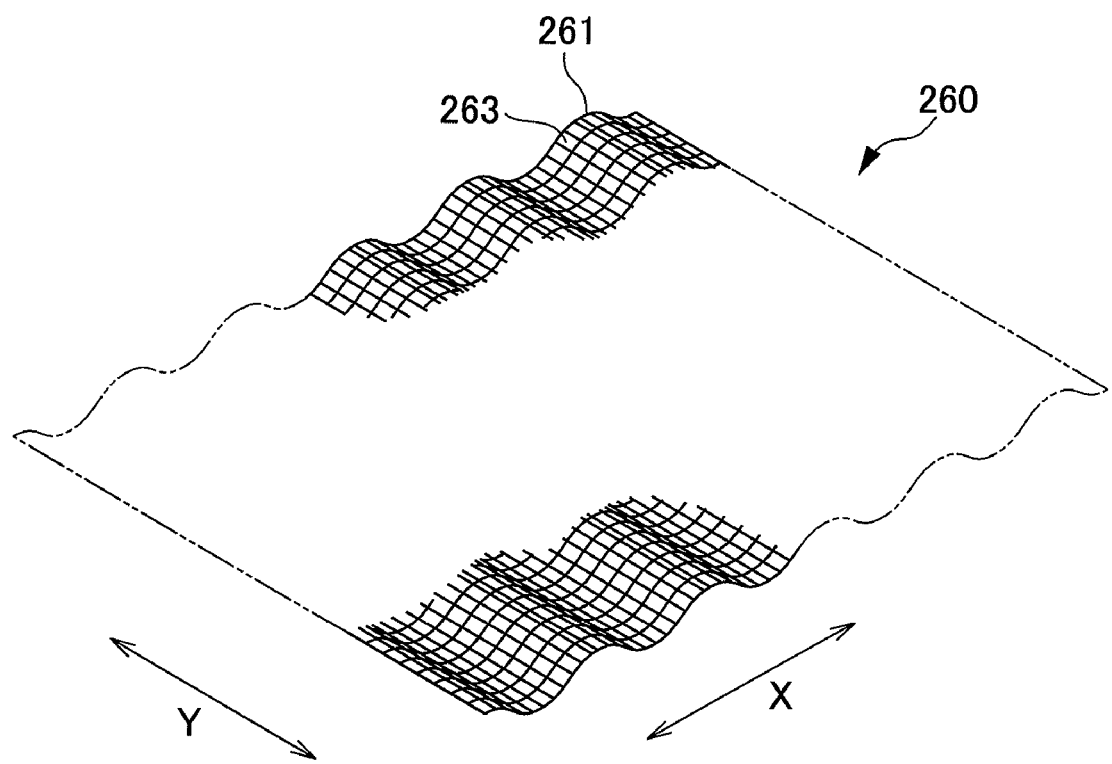
FIG. 12 shows an expanded perspective view of a net support member according to the third embodiment.

Referring to FIGS. 11 and 12, nonwoven fabric of the third embodiment of the present invention will be described.

2-2-1. Nonwoven Fabric

As shown in FIGS. 11 and 12, the present embodiment is different from the first embodiment in that entire nonwoven fabric 116 has rising and falling portions alternately formed to intersect one anther in a longitudinal direction (LD). Differences from the first embodiment will be mainly described below.

According to the embodiment, the nonwoven fabric 116 is formed so that the entire nonwoven fabric 116 has undulating portions in the longitudinal direction (LD).

2-2-2. Manufacturing Method

The nonwoven fabric 116 of the present embodiment can be formed as in the case of the first embodiment. However, a form of a net support member 260 which is an air-permeable support member 200 is different. According to the present embodiment, the net support member 260 is formed by interweaving a plurality of wires 261 of predetermined thicknesses which are not air permeable portions. By interweaving the plurality of wires 261 at predetermined spaces, it is possible to obtain a net support member 260 in which a plurality of holes 263 are formed as air permeable portions.

According to the present embodiment, for example, as shown in FIG. 12, the net support member 260 is formed so that corrugated rising and falling portions can be alternately formed in a direction parallel to a Y axis. The net support member 260 is a support member in which undulating portions are formed in a direction parallel to one of longitudinal and short directions.

The net support member 260 of FIG. 12 includes a plurality of small-diameter holes 263, and a gas directed from an upper surface side of a fiber web 100 is supplied without being blocked by the net support member 260. This net support member 260 does not greatly change a flow of the fluid, mainly consisting of gas, to be directed, and nor fibers 101 are moved in a lower direction of the net support member 260.

Similarly, as the net support member 260 includes undulating portions itself, by the fluid, mainly consisting of gas, directed from the upper surface side of the fiber web 100, the fiber web 100 is formed into a shape having undulating portions to match a shape of the net support member 260.

It is possible to form the nonwoven fabric 116 by moving the fiber web 100 in a direction of an X axis while directing the fluid, mainly consisting of gas, to the fiber web 100 mounted on the upper surface of the net support member 260.

A form of rising and falling in the net support member 260 can be optionally set. For example, a pitch between a rising and falling top in the direction of the X axis shown in FIG. 12 is 1 to 30 mm, preferably 3 to 10 mm. For example, a level difference between a top and a bottom of rising and falling portions in the net support member 260 is 0.5 to 20 mm, preferably 3 to 10 mm. As shown in FIG. 12, a sectional shape of the net support member 260 in the direction of the X axis is not limited to a waveform, but the sectional shape may be a shape in which rough triangles are connected to make sharp the top and the bottom of the rising and falling portions, or a shape in which rough squares are connected to make substantially flat the top and the bottom of the rising and falling portions.

The nonwoven fabric 116 of the present embodiment can be formed by the nonwoven fabric manufacturing apparatus 90. For a manufacturing method of the nonwoven fabric 116 in the nonwoven fabric manufacturing apparatus 90, the description of the manufacturing method of the nonwoven fabric 110 and the nonwoven fabric manufacturing method of the first embodiment can be referred to.

2-3. FOURTH EMBODIMENT

Figure 13:
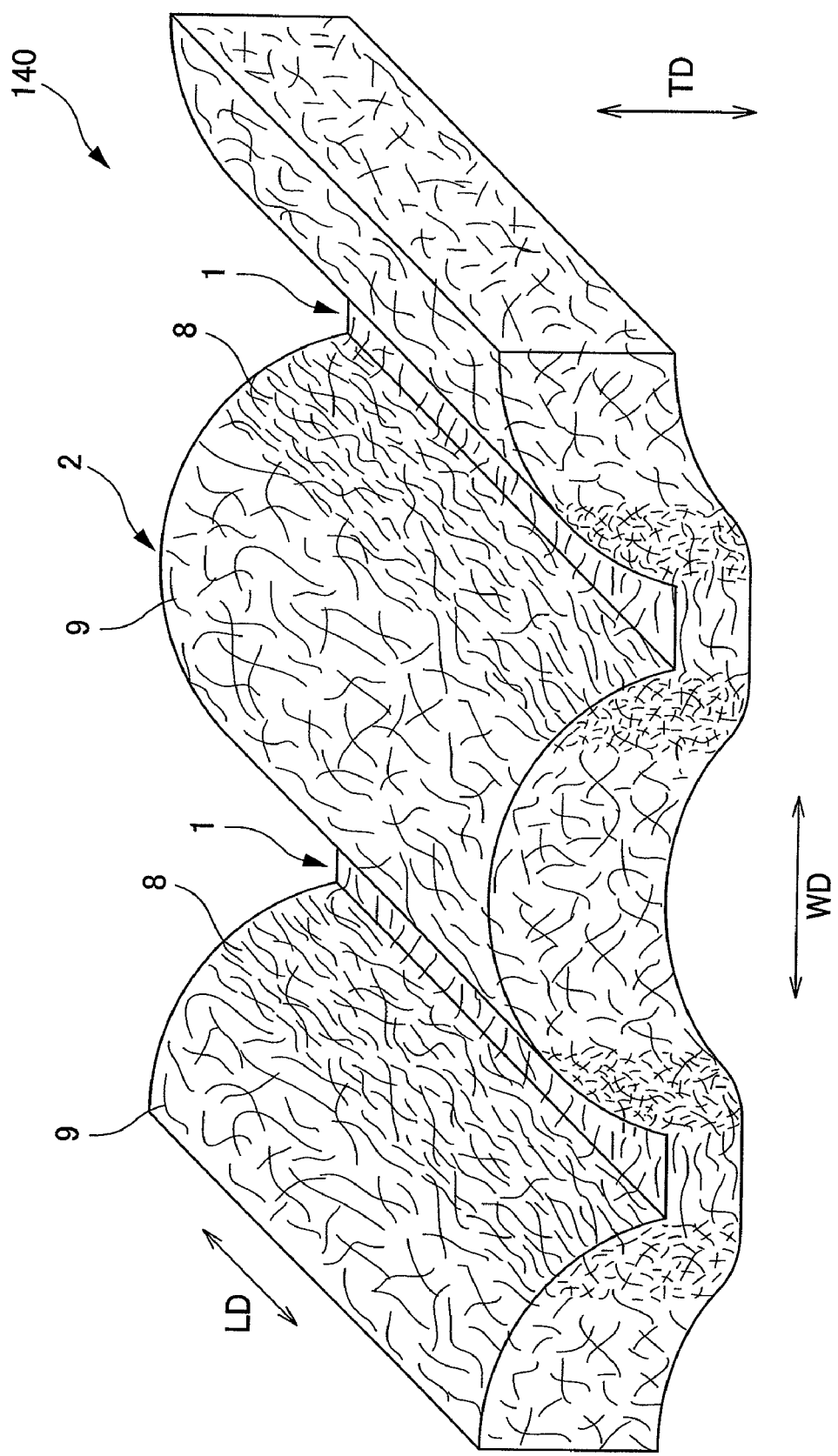
FIG. 13 shows an expanded perspective view of a nonwoven fabric according to a fourth embodiment.

Referring to FIG. 13, nonwoven fabric of the fourth embodiment of the present invention will be described.

As shown in FIG. 13, nonwoven fabric 140 of the present embodiment is different from that of the first embodiment in a form of an opposite surface which is the other surface side rather than the surface including a groove portion 1 and a convex portion 2 of the nonwoven fabric 140. Differences from those of the first embodiment will be described below.

2-3-1. Nonwoven Fabric

According to the present embodiment, the nonwoven fabric 140 includes groove portions 1 and convex portions 2 alternately formed in parallel on a first surface side. On a second surface side of the nonwoven fabric 140, an area which corresponds to the bottom of the convex portion 2 is formed so as to project to a projecting side of the convex portion 2. In other words, in the nonwoven fabric 140, on the second surface side thereof, an area which is a bottom of the convex portion 2 on the first surface side is recessed to form a concave portion. An area of the second surface side which is a bottom of the groove portion 1 of the first surface side projects in a direction opposed to the convex portion 2 of the first surface side to form a convex portion.

2-3-2. Manufacturing Method

According to the embodiment, a fiber web 100 is set on the net support member 210, the fiber web 100 is moved in a predetermined direction while directing a fluid, mainly consisting of gas, and the directed fluid, mainly consisting of gas, is sucked from the lower side of the net support member 210. Then, by setting the amount of a fluid, mainly consisting of gas, to be sucked (suction) so as to be less than that of the fluid, mainly consisting of gas, to be directed, the fluid, mainly consisting of gas, to be directed clashes with the net support member 210 and is slightly rebounded. Thus, the lower surface side (bottom surface side) of the convex portion 2 can be formed to project in the same direction of the convex portion 2 on the upper surface side of the convex portion 2. Accordingly, the amount of a fluid, mainly consisting of gas, to be directed should preferably be set to be greater than that of a fluid, mainly consisting of gas, to be sucked (suction). As a result, the area of the second surface side which is a bottom of the groove portion 1 relatively projects to form a convex portion projecting from the lower surface side.

A manufacturing method of the nonwoven fabric 140 of the present embodiment is similar to that of the first embodiment. For the support member used for manufacturing the nonwoven fabric 140, the same as the net support member 210 of the first embodiment can be used.

2-4 FIFTH EMBODIMENT

Figure 14:
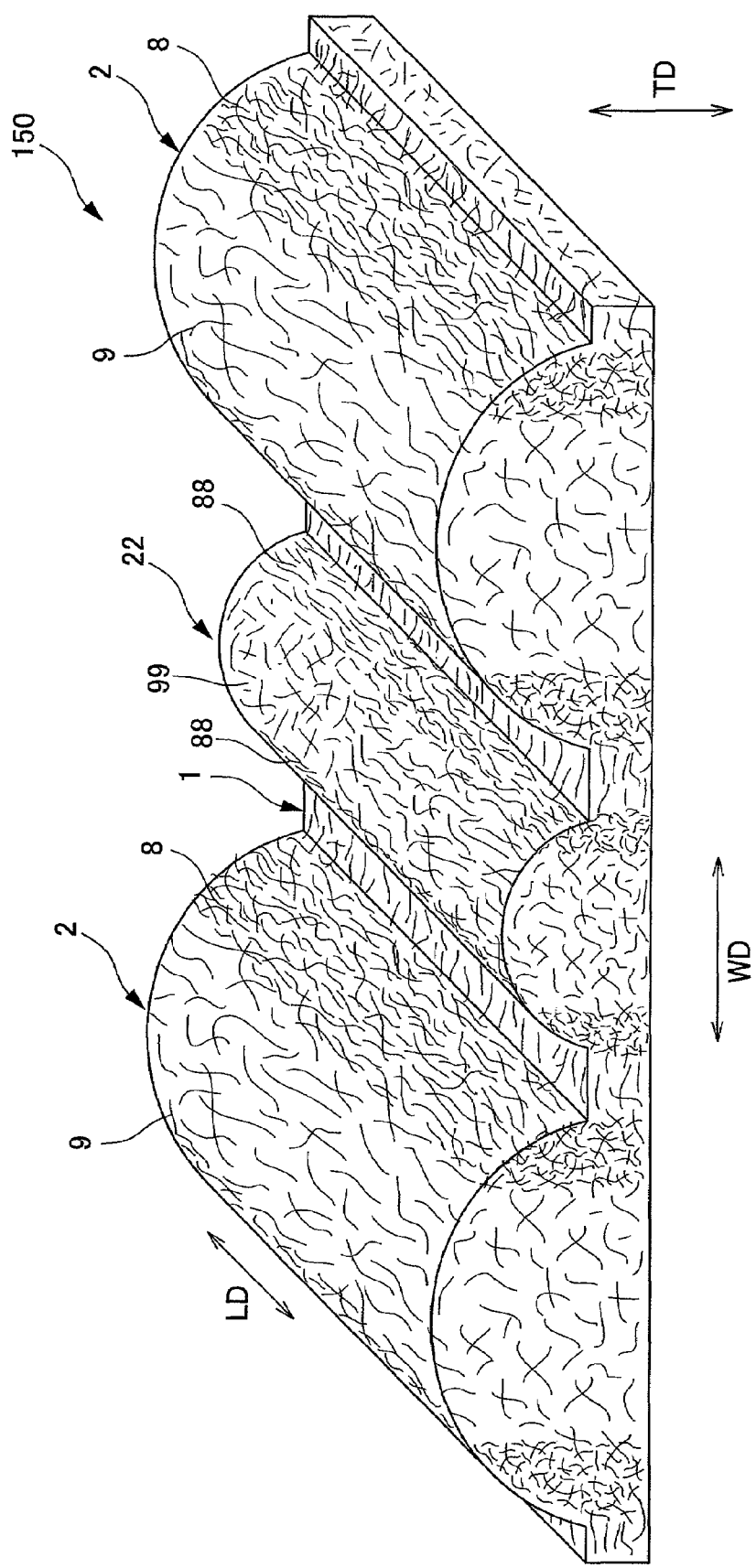
FIG. 14 shows an expanded perspective view of a nonwoven fabric according to a fifth embodiment.

Referring to FIG. 14, nonwoven fabric of the present embodiment will be described.

As shown in FIG. 14, nonwoven fabric 150 of the present embodiment is different from that of the first embodiment in that a second convex portion 22 having a different height from that of the convex portion 2 formed on a first surface side of the nonwoven fabric 150. Differences from the first embodiment will be mainly described below.

2-4-1 Nonwoven Fabric

The nonwoven fabric 150 includes a plurality of groove portions 1 formed in parallel on it's a first surface side. A plurality of convex portions 2 and a plurality of second convex portions 22 are alternately formed among each pair of the groove portion of the plurality of formed groove portions 1 respectively. The convex portions 2 and the second convex portions 22 are formed in parallel as in the case of the groove portions 1.

The convex portion 2 and the second convex portion 22 are areas in which no fluid, mainly consisting of gas, is directed in a fiber web 100, and the groove portions 1 are formed so that the convex portion 2 and the second convex portion 22 can relatively project. For example, the second convex portion 22 is formed to be lower than the convex portion 2 in a thickness direction (TD) of the nonwoven fabric 150, and smaller in a width direction (WD) as well. However, a fiber density, fiber orientation and a fiber basis weight of the second convex portion 22 are similar to those of the convex portion 2.

Regarding the convex portion 2 and the second convex portion 22 of the nonwoven fabric 150, the convex portions 2 or the second convex portions 22 are formed among each pair of the plurality of groove portions 1 formed in parallel. The convex portion 2 is formed to be adjacent to the second convex portion 22 sandwiching the groove portion 1. The second convex portion 22 is formed to be adjacent to the convex portion 2 sandwiching the groove portion 1. In other words, the convex portions 2 and the second convex portions 22 are alternately formed in a manner of sandwiching the groove portions 1. Specifically, the convex portion 2, the groove portion 1, the second convex portion 22, the groove portion 1, and the convex portion 2 are formed in this order by repeating this arrangement pattern. A positional relation between the convex portion 2 and the second convex portion 22 is not limited to this, but at least in a part of the nonwoven fabric 150, a plurality of convex portions 2 can be formed in a manner of sandwiching the groove portions 1. Similarly, a plurality of second convex portions 22 can be formed to be adjacent to each other sandwiching the groove portion 1.

For the fiber density of the second convex portion 22, as in the case of the convex portion 2 of the nonwoven fabric 150, longitudinally-oriented fibers of the groove portion 1 are collected on a side potion 88 of the second convex portion 22 by spray, thereby increasing a fiber density of the side potion 88 of the second convex portion 22. For fiber orientation of the side potion 88, a content of longitudinally-oriented fibers oriented in a longitudinal direction (LD) which is a longitudinal direction is greater than that of laterally-oriented fibers oriented in a width direction (WD) which is a horizontal direction. Thus, the fibers are oriented in a longitudinal direction as a whole. A central portion 99 sandwiched by the side potions 88 in the second convex portion 22 is formed such that its fiber basis weight is less than that of the side potion 88 but greater than that of the groove portion 1.

2-4-2. Manufacturing Method

According to a manufacturing method of the nonwoven fabric 150 of the present embodiment, a form of a blowing nozzles 913 of the nonwoven fabric manufacturing apparatus 90 used for manufacturing the nonwoven fabric is different.

A fiber web 100 set on an upper surface of a net support member 210 is moved in a predetermined direction while blowing a fluid, mainly consisting of gas, thereby forming nonwoven fabric 150. A groove portion 1, a convex portion 2, and a second convex portion 22 are formed while the fluid, mainly consisting of gas, is directed. Formation of these portions can be optionally changed according to a form of the blowing nozzles 913 of the fluid, mainly consisting of gas, in the nonwoven fabric manufacturing apparatus 90.

For example, to form the nonwoven fabric 150, the nonwoven fabric 150 can be manufactured by the nonwoven fabric manufacturing apparatus 90 in which spacing of the blowing nozzles 913 for blowing the fluid, mainly consisting of gas, is adjusted. For example, by setting the space of the blowing nozzles 913 to be less than that of the blowing nozzles 913 of the first embodiment, a second convex portion 22 that is lower in height than a convex portion 2 in a thickness direction (TD) can be formed. By setting the space of the blowing nozzles 913 to be greater than that of the blowing nozzles 913 of the first embodiment, a convex portion that is greater in height than the convex portion 2 in the thickness direction (TD) can be formed. Regarding spacing of forming the blowing nozzles 913, by arranging blowing nozzles 913 to alternate wide and narrow spaces, the nonwoven fabric 150 in which convex portions 2 and second convex portions 22 are alternately arranged in parallel sandwiching the groove portions 1 is formed. Spacing of the blowing nozzles 913 is not limited to this. Spaces can be optionally set according to the desired height of the convex portion and arrangement of the second convex portions 22 in nonwoven fabric to be formed.

The nonwoven fabric 150 of the present embodiment can be manufactured by the nonwoven fabric manufacturing apparatus 90 as described above. However, for other components in a manufacturing method of the nonwoven fabric 150 in the nonwoven fabric manufacturing apparatus 90, the description of the manufacturing method of the nonwoven fabric 110 and the nonwoven fabric manufacturing apparatus 90 of the first embodiment can be referred to.

2-5. SIXTH EMBODIMENT

Figure 15:
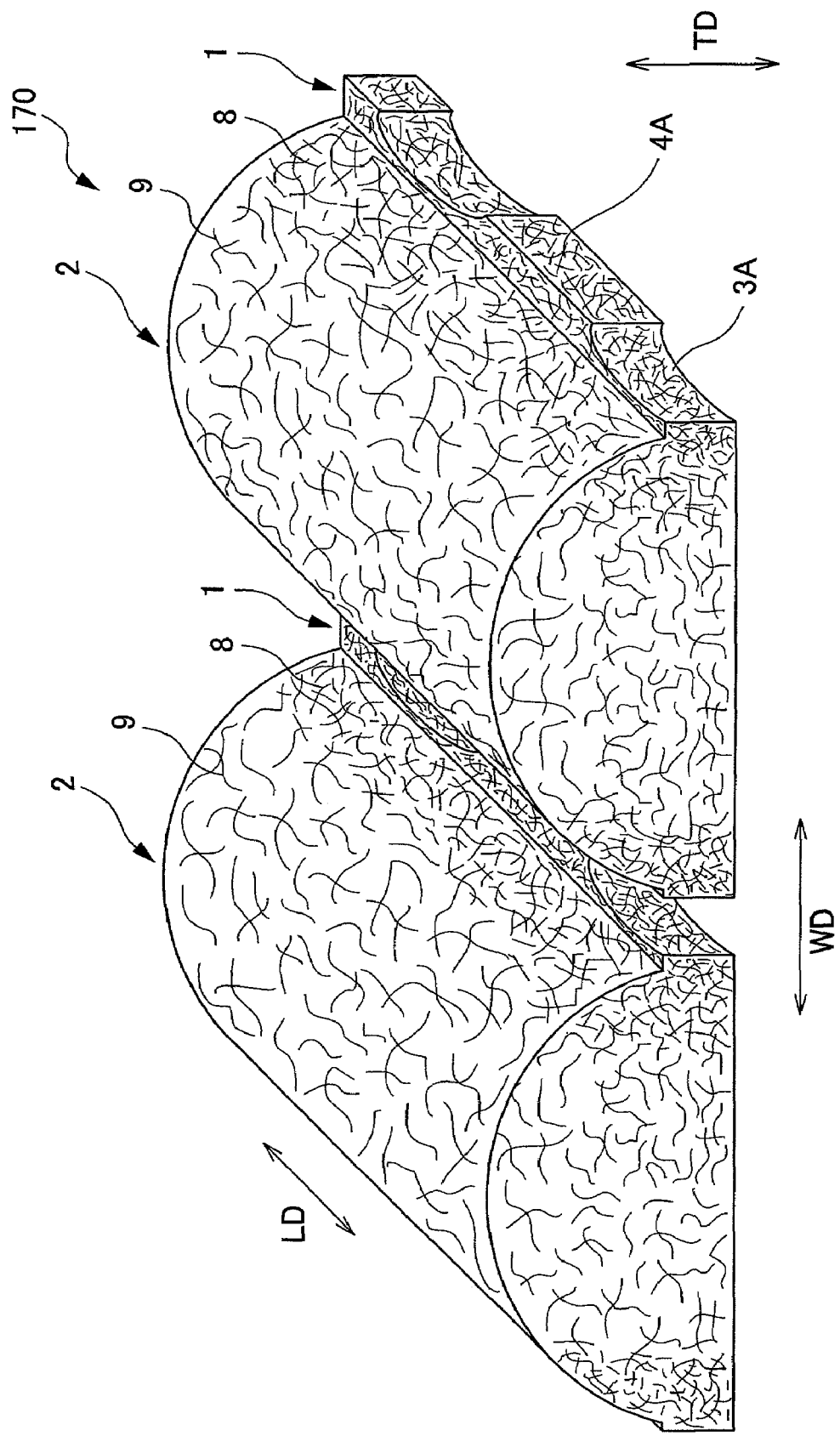
FIG. 15 shows an expanded perspective view of a nonwoven fabric according to a sixth embodiment.
Figure 16:
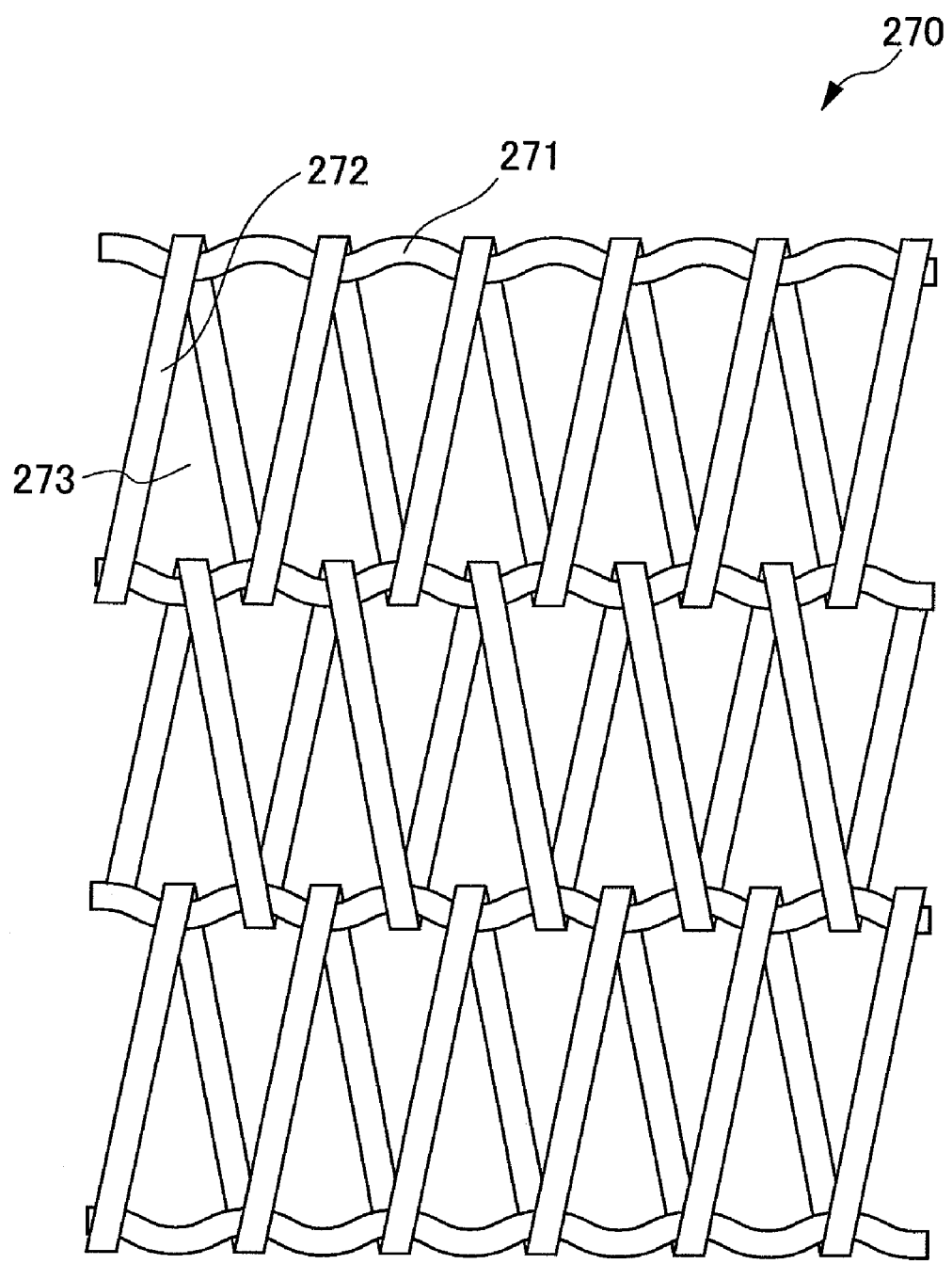
FIG. 16 shows an expanded plan view of a support member according to the sixth embodiment.

Referring to FIGS. 15 and 16, nonwoven fabric of the sixth embodiment of the present invention will be described.

As shown in FIGS. 15 and 16, the sixth embodiment is different from the first embodiment in that a recessed portion 3A and a projected portion 4A are formed in a groove portion 1 formed on a first surface side of nonwoven fabric 170. Differences will be mainly described below.

2.5.1 Nonwoven Fabric

As shown in FIG. 15, the nonwoven fabric 170 of the present embodiment is nonwoven fabric in which a plurality of groove portions 1 are formed in parallel at substantially equal spaces on a first surface side of the nonwoven fabric 170. A plurality of convex portions 2 are formed among each pair of the plurality of groove portions 1 respectively. In the groove portion 1, a plurality of recessed portions 3A, which are sparse areas with fiber densities that are less than that of the groove portion 1 are formed at substantially equal spaces. Among each pair of the plurality of recessed portions 3A, a plurality of projected portions 4A, which are areas other than the sparse areas are formed.

According to the present embodiment, the recessed portions 3A are formed at substantially equal spaces. Not limited to this, however, the recessed portions 3A may be formed at different spaces. In FIG. 15, the recessed portion 3A forms an opening. However, the recessed portion may not be an opening. Whether the recessed portion 3A becomes an opening or not depends on various conditions including the amount or strength of a fluid, mainly consisting of gas, to be directed, and a suction amount.

A height in the recessed portion 3A in a thickness direction (TD) of the nonwoven fabric 170 is no greater than 90% of a height in the projected portion 4A in the thickness direction (TD) of the nonwoven fabric, preferably 0 to 50%, more preferably 0 to 20%. A height of 0% means that the recessed portion 3A is an opening.

Lengths in longitudinal and width directions (LD and WD) per one recessed portion 3A are both 0.1 to 30 mm, preferably 0.5 to 10 mm. A pitch of the recessed portions 3A adjacent to each other sandwiching the projected portion 4A is 0.5 to 30 mm, preferably 1 to 10 mm.

A height in the projected portion 4A in the thickness direction (TD) of the nonwoven fabric 170 is no greater than that of a convex portion 2 in the thickness direction (TD) of the nonwoven fabric 170, preferably 20 to 100%, more preferably 40 to 70%.

Lengths in the longitudinal and width directions (LD and WD) per one projected portion 4A are both 0.1 to 30 mm, preferably 0.5 to 10 mm. A pitch of tops of the projected portions 4A adjacent to each other sandwiching the recessed portion 3A is 0.5 to 30 mm, preferably 1 to 10 mm.

A sectional shape of the projected portion 4A in the longitudinal direction (LD) of the nonwoven fabric is substantially square. The sectional shape of the projected portion 4A in the longitudinal direction (LD) is not limited to a substantially square shape, but any shapes such as a dome shape, a trapezoidal shape, a triangular shape, or an Ω-shape can be employed. To suppress spreading of a predetermined liquid in the groove portion 1, the sectional shape of the projected portion 4A in the longitudinal direction (LD) should preferably be substantially square. To prevent foreign object feelings caused by contact of the projected portion 4A with the skin under excessive external pressure, a top or a plane of the projected portion 4A is preferably curved.

For a sectional shape of the recessed portion 3A in the longitudinal direction (LD) of the nonwoven fabric, any shapes such as a dome shape, a trapezoidal shape, an Ω-shape, a square, or a shape reversed up and down of such shapes, can be employed. The recessed portion 3A should preferably be an opening. This is because even when excessive external pressure is applied, or a predetermined highly viscous liquid is brought to the nonwoven fabric 170, spreading of the predetermined liquid in the groove portion 1 can be suppressed.

Fibers of the projected portions 4A adjacent to each other sandwiching the recessed portion 3A in the groove portion 1 are oriented as a whole in a width direction (WD) of the groove portion 1.

When the recessed portion 3A is an opening, in an area which is an opening, longitudinally-oriented fibers are collected on the convex portion 2 side by a fluid mainly consisting of gas to be directed, and laterally-oriented fibers are collected on the projected portion 4A side. Accordingly, fibers 101 around the opening are oriented to surround the opening. Thus, even when external pressure is applied, crushing or clogging of the opening hardly occurs.

The projected portion 4A of the groove portion 1 is formed so that its fiber density is higher than that of the recessed portion 3A of the groove portion 1.

Fiber densities of the recessed portion 3A and the projected portion 4A can be freely adjusted according to various conditions including the amount of a fluid, mainly consisting of gas, and tension as in the case of the convex portion 2 and the groove portion 1 of the first embodiment. The recessed portion 3A may not be an opening.

The fiber density of the recessed portion 3A is preferably 0.0 to 0.10 g/cm$^3$. A fiber density of 0.0 g/cm$^3$ means that the recessed portion 3A is an opening. If a fiber density is greater than 0.20 g/cm$^3$, the predetermined liquid dropped in the groove portion 1 temporarily stays in the recessed portion 3A.

For example, when the nonwoven fabric 170 is used for a top sheet of an absorbent article, if an action change or the like occurs while the predetermined liquid stays in the recessed portion 3A, the predetermined liquid may easily leak from the recessed portion 3A and spread to the groove portion 1, and further spread to a surface of the nonwoven fabric 170 and soil the skin.

A fiber density of the projected portion 4A is 0.005 to 0.20 g/cm$^3$, preferably 0.007 to 0.10 g/cm$^3$. If the fiber density of the projected portion 4A is less than 0.005 g/cm$^3$, when excessive external pressure is applied to crush the convex portion 2, the projected portion 4A may be similarly crushed, reducing the space in the recessed portion 3A of the groove portion 1 in some cases.

On the other hand, if a fiber density of the projected portion 4A is greater than 0.20 g/cm$^3$, the predetermined liquid dropped in the groove portion 1 stays in the projected portion 4A. When application of excessive external pressure brings the nonwoven fabric 170 into direct contact with skin, a wet feeling may be imparted to the user.

The recessed portion 3A of the groove portion 1 is formed so that a fiber basis weight of the fibers 101 can be less than those of the convex portion 2 and the projected portion 4A. In other words, in the nonwoven fabric 170, the recessed portion 3A is formed so that a fiber basis weight can be lowest.

For example, the fiber basis weight of the recessed portion 3A is 0 to 100 g/m$^2$, preferably 0 to 50 g/m$^2$. A fiber basis weight of 0 g/m$^2$ means that the recessed portion 3A is an opening. If the fiber basis weight of the recessed portion 3A is greater than 100 g/m$^2$, the predetermined liquid dropped in the groove portion 1 temporarily stays in the recessed portion 3A. Accordingly, for example, when the nonwoven fabric 170 is used as a top sheet of an absorbent article, if an action change or the like occurs while the predetermined liquid stays in the recessed portion 3A, the predetermined liquid may easily leak from the recessed portion 3A to spread to the groove portion, and further spread to the surface of the nonwoven fabric 170 and soil the skin.

The projected portion 4A of the groove portion 1 is formed so that the fiber basis weight of the fibers 101 is greater than that of the recessed portion 3A. For example, a fiber basis weight of the projected portion 4A is 5 to 200 g/m$^2$, preferably 10 to 100 g/m$^2$. If a fiber basis weight of the projected portion 4A is less than 5 g/m$^2$, if excessive external pressure is applied to crush the convex portion 2, the projected portion 4A is similarly crushed, reducing the space of the recessed portion 3A in the groove portion 1 in some cases. If the fiber basis weight of the projected portion 4A is greater than 200 g/m$^2$, the predetermined liquid dropped in the groove portion 1 stays in the projected portion 4A. When application of excessive external pressure brings the nonwoven fabric 170 into direct contact with skin, a wet feeling may be imparted on the user.

2-5-2. Manufacturing Method

A method for manufacturing the nonwoven fabric 170 will be described below. First, as in the case of the first embodiment, a fiber web 100 is set on an upper surface side of a support member 270 of FIG. 16 which is an air permeable support member. In other words, the fiber web 100 is supported from a lower side by the support member 270.

Then, the fiber web 100 is moved in a predetermined direction while it is supported by the support member 270. By directing a fluid, mainly consisting of gas, to an upper surface side of the moving fiber web 100, the nonwoven fabric 170 can be manufactured.

For example, the support member 270 is a spirally woven air permeable net formed by alternately winding wires 272 of predetermined thicknesses spirally on wires 271 of predetermined thicknesses arrayed substantially in parallel to bridge the plurality of wires 271.

The wires 271 and 272 of the support member 270 are not air permeable portions. Portions of the support member 270 surrounded with the wires 271 and 272 are holes 273.

In the case of such a support member, by partially changing weaving, thread size or thread shape, air permeable of the support member can be modified. For example, a support member 270 in which the wire 271 is a stainless circular thread, the wire 272 is a stainless flat thread, and these threads are spirally woven can be used.

For the wires 271 and 272 which are not air permeable portions, for example, a plurality of wires (e.g., two) may be twisted together to form a wire 271 or 272, and a space may be generated between the twisted wires to supply a fluid, mainly consisting of gas, to a part.

In this case, air permeability of the wires 271 and 272 (especially wire intersecting part) which are not air permeable portions is no greater than 90% of that of the hole 273 which is an air permeable portion, preferably 0 to 50%, more preferably 0 to 20%. An air permeability of 0% means that the fluid, mainly consisting of gas, can not be supplied in effect.

For example, air permeability of an area such as the hole 273 which is an air permeable portion is 10000 to 60000 cc/cm$^2$·minute, preferably 20000 to 50000 cc/cm$^2$·minute. However, for example, when another air permeable support member such as a metal plate is bored to form an air permeable portion, resistance of the fluid, mainly consisting of gas, to the plate portion is eliminated. Thus, the air permeability may be no less than the aforementioned numerical value.

In the support member, the area which is not an air permeable portion should preferably have surface slippage that is greater than that of the area which forms the air permeable portion. The high slippage facilitates movement of the fibers 101 in an area in which the area having the fluid, mainly consisting of gas, directed thereto and the non air permeable portion intersect each other. As a result, it is possible to enhance the ability to mold the recessed portion 3A and the projected portion 4A.

When the fluid, mainly consisting of gas, is directed to the fiber web 100 supported by the support member 270, the area to which the fluid, mainly consisting of gas, has been directed becomes a groove portion 1. Because of the formation of the groove portion 1, a portion which relatively projects becomes a convex portion 2. Formation of the groove portion 1 and the convex portion 2 is as described in the first embodiment.

In the groove portion 1, when the fluid mainly consisting of gas is directed to the intersection portion of the wires 271 and 272 in the support member 270, the fluid, mainly consisting of gas, is bounced on the intersection portion. Accordingly, the fibers 101 supported on the intersection portion are collected back and forth and left and right to form a recessed portion 3A.

The fluid, mainly consisting of gas, is directed to the area in the upper surface of the holes 273 of the support member 270 in the groove portion 1 to form a groove portion 1, and a recessed portion 3A is formed in the groove portion 1 to form a projected portion 4A which relatively projects.

In the recessed portion 3A, by directing the fluid, mainly consisting of gas, the fibers 101 that become oriented substantially parallel to the groove portion 1 are collected on the convex portion 2 side, and the fibers 101 oriented in a direction (horizontal direction) intersecting a direction along the groove portion 1 are collected on the projected portion 4A side. Thus, a fiber basis weight is formed to be low in the recessed portion 3A.

On the other hand, in the projected portion 4A, the fibers 101 are collected from the recessed portion 3A, and thus a fiber basis weight is formed to be greater than that of the recessed portion 3A.

According to another method for manufacturing the nonwoven fabric 170, nonwoven fabric including a groove portion 1 and a convex portion 2 may first be manufactured as in the case of the first embodiment, and then the groove portion 1 may be embossed to form a recessed portion 3A and a projected portion 4A, thereby manufacturing nonwoven fabric 170. A relation in fiber density or fiber basis weight between the recessed portion 3A and the projected portion 4A in this case may be reverse to that of the embodiment. In other words, a fiber density and a fiber basis weight of the projected portion 4A may be less than those of the recessed portion 3A.

According to another method for manufacturing the nonwoven fabric 170, concave and convex portions such as a convex portion 2 and a groove portion 1 may be formed beforehand in the fiber web 100, another fiber web having freedom among fibers is stacked on the fiber web 100, and a fluid, mainly consisting of gas, may be spayed thereto. Then, by the spayed fluid, mainly consisting of gas, a convex portion and a groove portion are formed in the upper fiber web. However, in the groove portion, concave and convex portions formed in the lower fiber web are exposed because of a low fiber basis weight to form a projected portion and a recessed portion of the embodiment. Subsequently, heat treatment is carried out to integrate the upper and lower fiber webs.

The nonwoven fabric 170 of the present embodiment can be manufactured by the nonwoven fabric manufacturing apparatus 90. For a manufacturing method of the nonwoven fabric 170 in the nonwoven fabric manufacturing apparatus 90, the description of the manufacturing method of the nonwoven fabric 110 and the nonwoven fabric manufacturing apparatus 90 of the first embodiment can be referred to.

3. EMBODIMENT

3-1. First Embodiment

Fiber Structure

Fiber A has a core-in-sheath structure of low density polyethylene (melting point of 110 degrees) and polyethylene terephthalate, has an average fineness of 3.3 dtex and an average fiber length of 51 mm, and is coated with hydrophilic oil solution. Fiber B has a core-in-sheath structure of high density polyethylene (melting point of 135 degrees) and polyethylene terephthalate and is different to fiber A in that fiber B is coated with water-repellent oil solution. Then, a fiber assembly was obtained by mixing the fiber A mixed with the fiber B to provide a cotton mixture. The fiber A was mixed with the fiber B with a mixing ratio of 70:30. The fiber assembly had a basis weight of 40 g/m$^2$.

Sheath components of the fiber A and the fiber B are different in the melting point to cause the fibers to have different strengths at the intersecting point, thus providing the nonwoven fabric with an improved softness. Specifically, when the fiber assembly is subjected to an oven having a temperature of 120 degrees C. for example, low density polyethylene at intersecting points of the fibers A and the intersecting point of the fiber A and the fiber B melts. Thus, the fibers are heat-sealed to one another and the intersecting points of the fibers A including a larger amount of melt low density polyethylene have a greater strength. The high density polyethylene at intersecting points of the fibers B does not melt and is thus not heat-sealed. Specifically, the relation for the intersecting point strength between the fiber A and the fiber B is that the intersecting points of the fiber A has a greater strength than that of the strength of the intersecting points of the fiber A and the fiber B and the intersecting points of the fibers A and the fiber B has a higher strength than that of the intersecting points of the fibers B.

Manufacture Conditions

The blowing nozzles 913 in FIG. 9 are structured to have a diameter of 1.0 mm and a pitch thereamong of 6.0 mm. Each of the blowing nozzles 913 has a substantially circle shape. A vent pipe in the blowing unit 910 connecting the blowing nozzles 913 allows fluid, mainly consisting of gas, to pass there through and has a circular cylinder cross sectional shape. The blowing unit 910 has a width of 500 mm. Hot air was blown to the fiber web having the above structure at a temperature of 105 degrees C. and an air volume of 1200 L/min.

The fiber assembly having the above-described fiber structure is spread-fibered by a card machine having a speed of 20 m/min to prepare a fiber web. Then, the fiber web is cut to have a width of 450 mm. Then, the fiber web is transferred on an air permeable net (20 mesh) with a speed of 3 m/min. While the fiber web is being blown with hot air based on the manufacture conditions by the blowing unit 910 and the blowing nozzles 913 as described above, air is sucked from the lower side of the air permeable net with an amount of air suctioned being less than the amount of blown hot air. Thereafter, the fiber web is transferred through an oven having a temperature of 125 degrees C. and hot blast air amount of 10 Hz, for approximately 30 seconds while the fiber web being transferred by the air permeable net.

Result

Convex portions: The resultant convex portion showed a basis weight of 51 g/m$^2$, a thickness of 3.4 mm (thickness from an apex of the convex portions to the back face of the convex portions at the apex of 2.3 mm), and a fiber density of 0.03 g/cm$^3$. One convex portion showed a width of 4.6 mm and a pitch of 5.9 mm.

Groove: The resultant the groove portion showed a basis weight of 24 g/m$^2$, a thickness of 1.7 mm, and a fiber density of 0.01 g/cm$^3$. One groove portion showed a width of 1.2 mm and a pitch of 5.8 mm.

Shape: The resultant shape showed the back face of the groove portion at the lowermost face of the nonwoven fabric. The back face of the convex portion protruded in the same direction as that of the convex portion and was formed not to constitute the lowermost face of the nonwoven fabric. The convex portion had a substantially dome-like cross sectional shape and a convex portion and a groove portion were continuously formed along the longitudinal direction (LD). A convex portion and a groove portion were formed so as to be repeated in the width direction (WD). Furthermore, the uppermost surface of the convex portion was structured so that intersecting point strengths of fibers are partially superposed so that the lowest fiber density is caused compared with the fiber density of nonwoven fabric formed in another embodiment (which will be described later).

3-2. Second Embodiment

Fiber Structure

Fibers used in the second embodiment have the same structure as that of the first embodiment.

Manufacture Conditions

A fiber web having the above-described fiber structure was placed on an air permeable net. Then, the fiber web was transferred in an oven having a temperature of 125 degrees C. and hot blast air amount of 10 Hz, for approximately 30 seconds. Immediately after being taken out from the oven (after about two seconds), the fiber web was blown with hot air a temperature 120 degrees C. and an air volume of 2200 L/minute by the above-described blowing unit 910 and blowing nozzles 913.

Result

Convex portions: The resultant convex portion showed a basis weight of 34 g/m$^2$, a thickness of 2.8 mm, and a fiber density of 0.04 g/cm$^3$ (thickness from an apex of the convex portion to the back face of the convex portion at the apex of 2.3 mm). One convex portion showed a width of 4.0 mm and a pitch of 6.1 mm.

Grooves: The resultant the groove portions showed a basis weight of 21 g/m$^2$, a thickness of 1.1 mm, and a fiber density of 0.02 g/cm$^3$. One groove portion showed a width of 2.1 mm and a pitch of 6.1 mm.

Shape: The resultant shape showed a convex portion and a groove portion.

3-3. Third Embodiment

Fiber Structure

Fibers used in the third embodiment have the same structure as that of the first embodiment.

Manufacture Conditions

While a fiber web was being blown with hot air with a temperature of 105 degrees C. and an air volume of 1000 L/min by the above-described blowing unit 910 and blowing nozzles 913, air was sucked from the lower side of the air permeable net with substantially the same amount as or a slightly greater amount than that of the blown hot air.

Result

Convex portions: The resultant convex portion showed a basis weight of 49 g/m$^2$, a thickness of 3.5 mm, and a fiber density of 0.02 g/cm$^3$. One convex portion showed a width of 4.7 mm and a pitch of 6.1 mm.

Grooves: The resultant groove portion showed a basis weight of 21 g/m$^2$, a thickness of 1.8 mm, and a fiber density of 0.01 g/cm$^3$. One groove portion showed a width of 1.4 mm and a pitch of 6.1 mm.

Shape: The resultant shape showed a convex portion and a groove portion. The convex portion showed a back face having a substantially flat shape so as to have a contact with the lower side.

3-4 Fourth Embodiment

Fiber Structure

Fibers used in the fourth embodiment have the same structure as that of the first embodiment.

Manufacture Conditions

A fiber web was blown with airflow by the above-described blowing unit 910 and blowing nozzles 913 under conditions of a temperature of 80 degrees C. and an air volume of 1800 L/min. Then, the fiber web having the above-described fiber structure was subjected to penetrations by needles arranged in a staggered manner with a pitch of 5 mm in the longitudinal direction (LD) and a pitch of 5 mm in the width direction (WD) with a speed of 200 penetrations/min while the fiber being moved in the longitudinal direction (LD) with a speed of 3 m/min, thereby causing fibers to be halfway interlaced. Thereafter, the fiber web was blown with airflow under manufacture conditions by the above-described blowing unit 910 and blowing nozzles 913 while air is sucked from the lower side of the air permeable net in substantially the same amount as or a slightly higher amount than that of the hot air.

Result

Convex portions: The resultant convex portion showed a fiber basis weight of 45 g/m$^2$, a length in the thickness direction of 2.3 mm, and a fiber density of 0.02 g/cm$^3$. One convex portion showed a width of 4.3 mm and a pitch of 5.8 mm.

Grooves: The resultant groove portion showed a fiber basis weight of 17 g/m$^2$, a thickness of 0.8 mm, and a fiber density of 0.02 g/cm$^3$. One groove portion showed a width of 1.0 mm and a pitch of 5.9 mm.

Shape: The resultant shape showed a convex portion and a groove portion continuously formed so as to be extended in the longitudinal direction (LD). The convex portion and the groove portion have an interlace point being partially directed in the lower direction and were continuously repeated in the width direction (WD).

4. Illustrative Application

The nonwoven fabric of the present invention can be used, for example, as a surface sheet for an absorbent article such as a sanitary napkin, liner or diaper. In this case, the convex portion may be provided in a skin-side face or in a back face. However, the convex portion provided in a skin-side face may reduce an area at which the nonwoven fabric has a contact with skin and thus a wet feeling due to body fluid may be suppressed. The nonwoven fabric of the present invention also can be used as an intermediate sheet between a surface sheet of an absorbent article and absorber material. In this case, an area at which skin has a contact with the surface sheet or the absorber material is reduced and thus body fluid is suppressed from returning from the absorber material to skin. The nonwoven fabric of the present invention also can be used as a side sheet of an absorbent article, an outermost surface of a diaper (outer back), or a female tape of a hook fastener tape for example because the nonwoven fabric of the present invention can reduce an area having a contact with skin and can provide a cushion feeling. The nonwoven fabric of the present invention also can be used for various products such as a wiper sheet for removing dust or scurf attached to a human body for example, a mask, or a mother milk pad.

4-1. Surface Sheet of Absorbent Article

Figure 17:
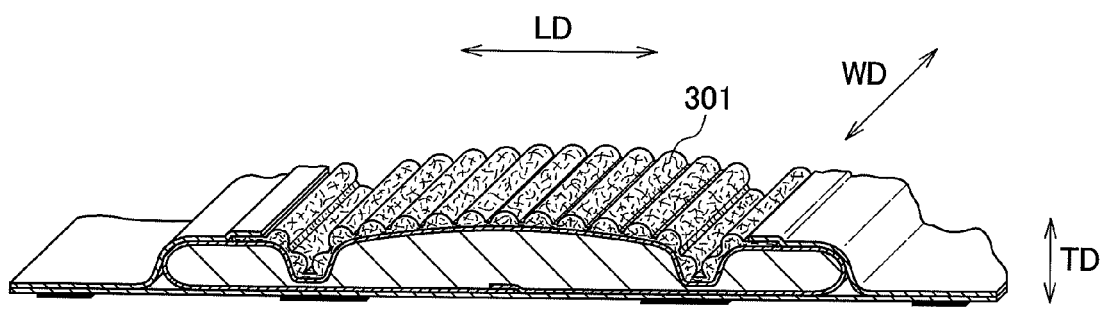
FIG. 17 shows a perspective sectional view of a sanitary napkin when the nonwoven fabric of the present invention is used as a top sheet.
Figure 18:
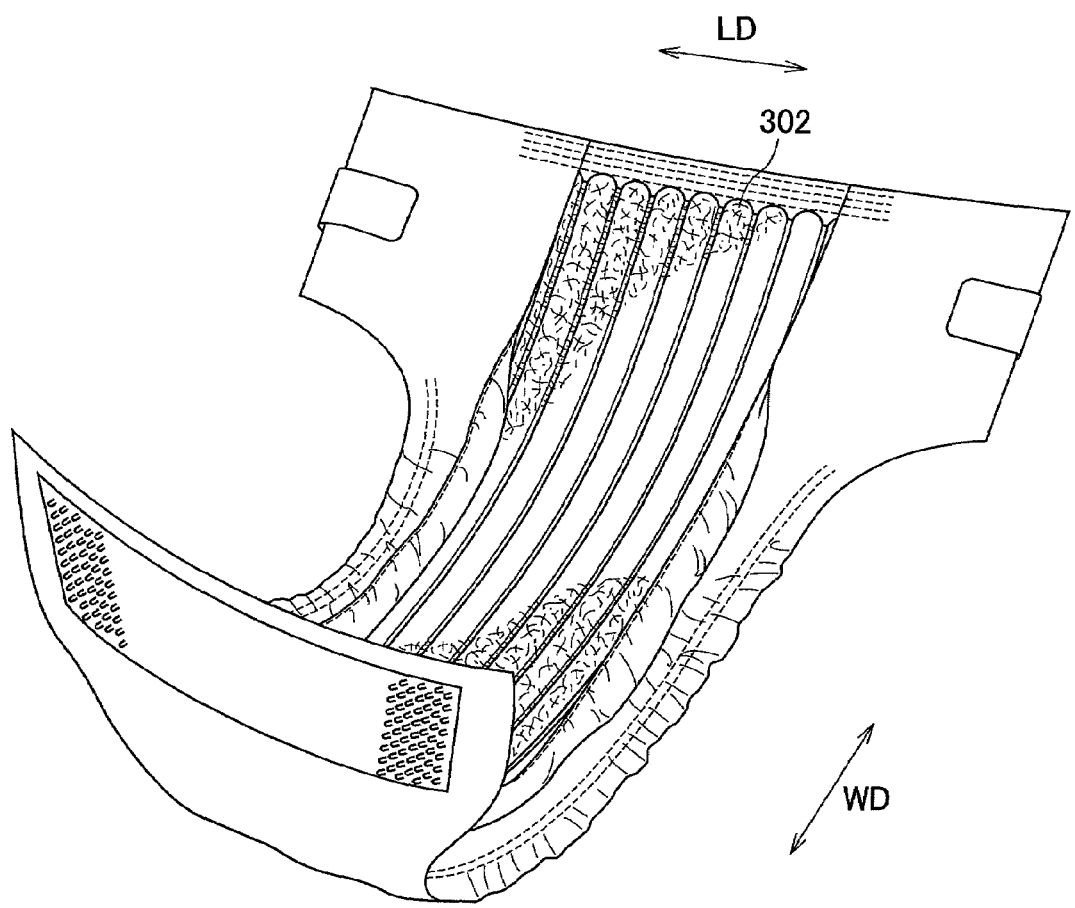
FIG. 18 shows a perspective view of a diaper when the nonwoven fabric of the present invention is used as an top sheet.

The nonwoven fabric of the present invention can be exemplarily used as surface sheets 301 and 302 of an absorbent article as shown in FIG. 17 and FIG. 18 for example. The surface sheets 301 and 302 have convex portions and groove portions arranged so that the groove portions have a smaller fiber basis weight than that of the convex portions. In this case, the nonwoven fabric is preferably arranged so that a surface including the convex portions faces to a human skin side.

When the nonwoven fabric is used as the surface sheets 301 and 302 for an absorbent article, predetermined liquid excreted to the absorbent article is mainly delivered to the groove portions. The nonwoven fabric of the present invention is structured so that the groove portion has a small fiber basis weight. Specifically, a small number of fibers provided in a unit area allows the liquid to be immediately transferred because the liquid can permeate there through while being less inhibited.

Furthermore, most fibers in the groove portion oriented in the width direction (WD) provide a high tensile strength in the width direction (WD) to prevent, even when the groove portion has a small fiber basis weight, a situation where the surface sheets 301 and 302 are broken due to friction in the width direction (WD) while the absorbent article being worn by a user for example.

On the other hand, the convex portion has a relatively higher fiber basis weight. The reason is that the groove portion is formed by moving fibers by fluid, mainly consisting of gas, to use the moved fibers to form a side area of the convex portion. The side area of the convex portion has closely-spaced fibers and thus has high rigidity. Furthermore, the center area at the convex portion sandwiched by the side portion includes a large amount of fibers oriented in the thickness direction (TD). This prevents, even when a load is applied to the convex portions, the convex portions from being easily crushed and, even when the convex portions are crushed by a load, the convex portions have a high compression recovery characteristic.

This can maintain a small area having a contact with skin even when the posture of a user changes to change a load applied to the surface sheets 301 and 302. Thus, an intended tactile sensation can be maintained and, even when liquid once absorbed by the absorber material returns to skin, the liquid is suppressed from being reattached to skin.

4-2. Intermediate Sheet of Absorbent Article

Figure 19:
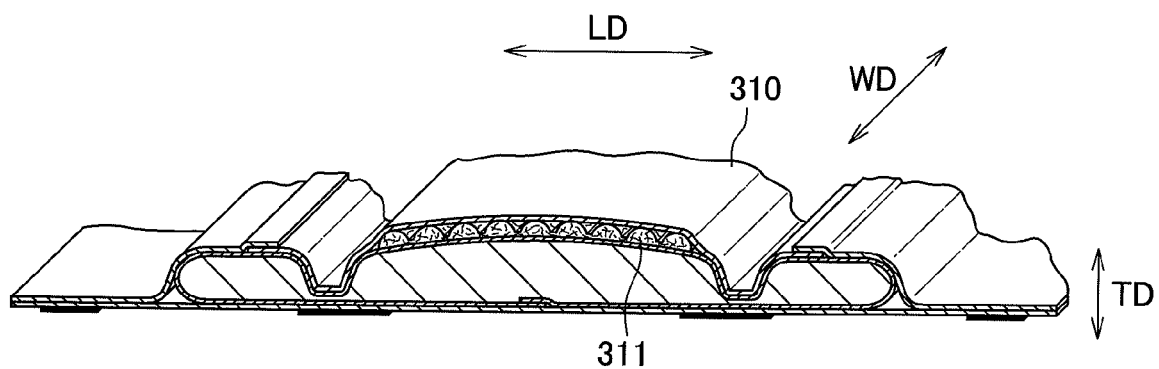
FIG. 19 shows a perspective sectional view of an absorbent article when the nonwoven fabric of the present invention is used as a middle sheet.

The nonwoven fabric of the present invention also can be exemplarily used, as shown in FIG. 19, as an intermediate sheet 311 for an absorbent article for example. The intermediate sheet 311 is structured so that a groove portion and a convex portion are provided and the groove portion has a relatively small fiber density. In this case, the nonwoven fabric is preferably arranged so that a surface including the convex portion is at the surface sheet 310.

By placing the nonwoven fabric as the intermediate sheet 311 so that a surface including the convex portions is at the surface sheet 310 side, the surface sheet 310 and the intermediate sheet 311 can have there between a plurality of spaces. Thus, even a large amount of liquid to the article within a short time can permeate there through while being less inhibited. Thus, the liquid can be prevented from returning to the surface sheet 310 to expand in a wide area.

Even when liquid passed the intermediate sheet 311 and absorbed by the absorber material returns to skin, a low ratio of the contact between the intermediate sheet 311 and the surface sheet 310 suppresses the liquid from returning to the surface sheet 310 to be attached to skin in a wide area.

The center part of the convex portion of the intermediate sheet 311 includes fibers oriented in the thickness direction (TD) in a larger amount than those in the side section and the groove portion and the intermediate sheet 311 has a convex portion having an apex that has a contact with the surface sheet 310. Thus, liquid left on the surface sheet 310 can be easily absorbed in the thickness direction (TD). This suppresses the liquid from being left on the surface sheet 310.

Thus, the surface sheet 310 can have a spot property and causes less residual liquid thereon. Thus, liquid can be prevented from being attached to skin for a long time. Furthermore, the side area of the convex is mainly composed of moved fibers. Thus, the side area includes longitudinal orientation fibers oriented in the longitudinal direction (LD) with a high inclusion rate. Thus, liquid (e.g., menstrual blood) delivered from the surface sheet 310 to the side area of the intermediate sheet 311 can be guided in the longitudinal direction (LD). This prevents, even when liquid is dispersed in the width direction (WD), the liquid from leaking from the absorbent article, thus improving the absorption efficiency of the absorber material.

4.3 Outer Back of Absorbent Article

Figure 20:
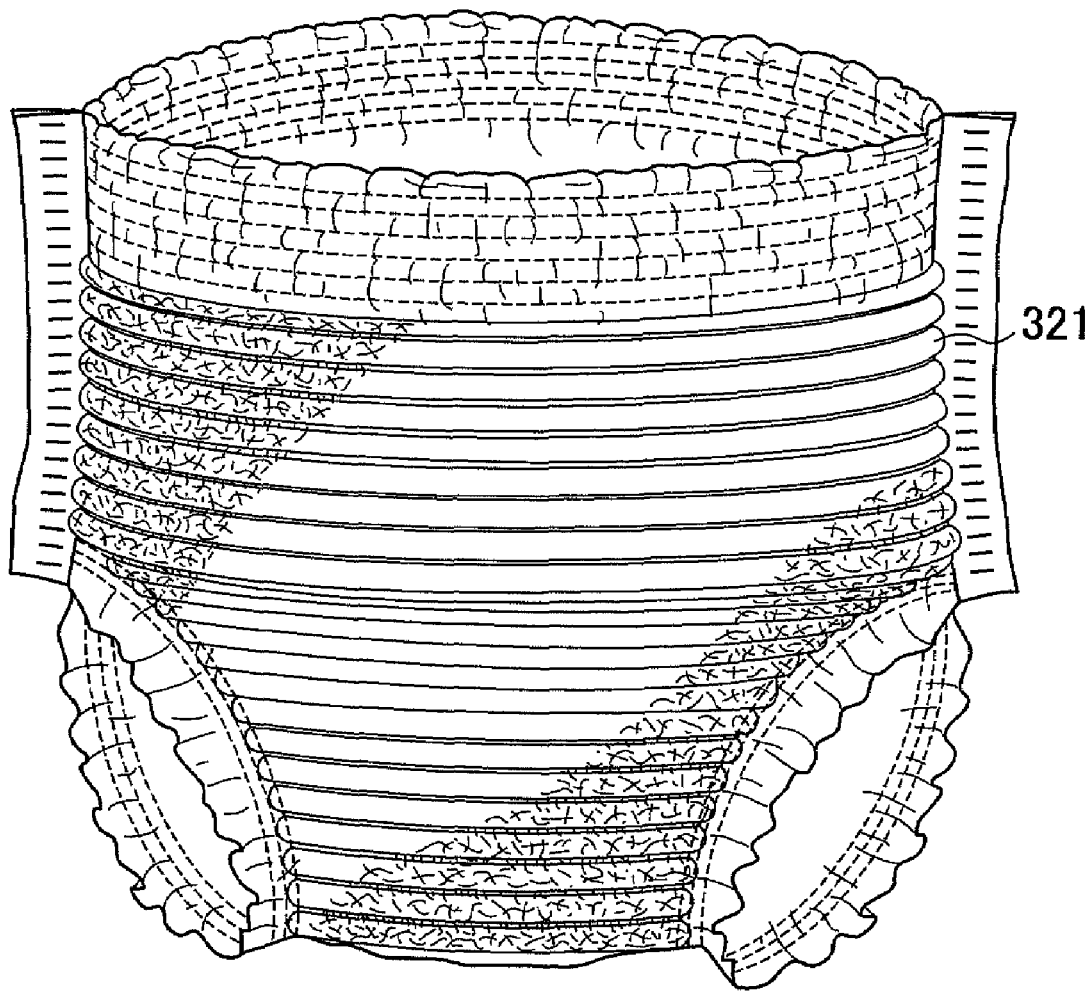
FIG. 20 shows a perspective view of an absorbent article when the nonwoven fabric of the present invention is used as an outer surface.

The nonwoven fabric of the present invention also can be exemplarily used as an outer surface (outer back 321) for an absorbent article (e.g., diaper) as shown in FIG. 20, for example. The outer back 321 is structured so that groove portions and convex portions are provided and the groove portion has a relatively low fiber density. In this case, the nonwoven fabric is preferably arranged so that a surface including the convex portion is at the outer side of the absorbent article.

The outer back 321 is structured so that the surface including the convex portion is at the outer side of the absorbent article. Thus, when a hand touches the absorbent article for the use for example, an improved feeling can be provided to the hand. The groove portion has a low fiber density and thus superior air permeability is obtained.

5. Constituting Members

The following section will describe in detail the respective constituting members of the nonwoven fabric of the present invention.

5-1. Nonwoven Fabric

5-1-1. Fiber Assembly

A fiber assembly is provided to have a substantially sheet-like shape and is structured to include fibers having a degree of freedom to move. In other words, fibers in a fiber assembly have a degree of freedom to one another. The term "degree of freedom to one another" herein means that fibers constituting a fiber web as a fiber assembly can be freely moved by fluid, mainly consisting of gas. This fiber assembly can be obtained, for example, by blowing mixed fibers including a plurality of fibers to form a fiber layer having a predetermined thickness. This fiber assembly can be obtained, for example, by blowing, a plurality of times, respective plurality of different fibers to form fiber layers.

A fiber assembly of the present invention may exemplarily be, for example, a fiber web formed by the card method or a fiber web not yet heat-sealed to solidify fibers. A fiber assembly of the present invention also may exemplarily be, for example, a web made by the air-laid method or a fiber web not yet heat-sealed to solidify fibers. A fiber assembly of the present invention also may exemplarily be, for example, a fiber web that is embossed by the point bond method and that is not yet heat-sealed to solidify fibers. A fiber assembly of the present invention also may exemplarily be, for example, a fiber assembly that is spun by the span bond method and that is not yet embossed or a fiber assembly that is embossed and that is not yet heat-sealed to solidify fibers. A fiber assembly of the present invention also may exemplarily be, for example, a fiber web that is formed by the needle punch method and that is halfway interlaced. A fiber assembly of the present invention also may exemplarily be, for example, a fiber web formed by the span lace method and that is halfway interlaced. A fiber assembly of the present invention also may exemplarily be, for example, fiber web that is spun by the melt blown method and that is not yet heat-sealed to solidify fibers. A fiber assembly of the present invention also may exemplarily be, for example, a fiber assembly in which fibers are not yet solidified by solvent provided by the solvent welding method.

A fiber assembly in which fibers can be easily re-arranged by air (gas) may preferably be a fiber web having a relatively long fiber that is made by the card method or a fiber web having fibers having a high freedom degree to one another and having a not yet heat-sealed web provided only by interlacing. In order to provide nonwoven fabric by forming groove portions (concavities and convexities) by a plurality of air (gas) flows to subsequently retain the shapes, the through air method is preferred according to which a predetermined heating apparatus for example is used to heat a fiber assembly by an oven processing (heat processing) to heat-seal thermoplastic fibers included in the fiber assembly.

5-1-2. Fibers

Fibers constituting a fiber assembly (e.g., the fibers 101 constituting the fiber web 100 shown in FIG. 1) may be, for example, thermoplastic resin (e.g., low density polyethylene, high density polyethylene, straight-chain polyethylene, polypropylene, polyethylene terephthalate, modified polypropylene, modified polyethylene terephthalate, nylon, polyamide) and the respective resins may be used separately or as a complex.

Such fibers may be combined to have a complex shapes such as the core-in-sheath type in which the core component has a higher melting point than that of the sheath component, the core-in-sheath eccentric core type, or the side-by-side-type in which left and right components have different melting points. Alternatively, other shapes also may be used such as a variant type (e.g., hollow type, flat type, Y-type, C-type). Alternatively, fibers constituting the fiber assembly also may be mixed with a three-dimensional crimp fiber (e.g., latent crimp, visible crimp) or a divided fiber divided by a physical load such as aqueous stream, heat, or embossing.

In order to form a three-dimensional crimp shape, predetermined visible crimp fiber or latent crimp fiber can be mixed. The term "three-dimensional crimp shape" herein means a spiral shape, a zigzag shape, an Ω-like shape for example in which fibers are mainly oriented in the flat surface direction but some fibers are oriented in the thickness direction. As a result, the yielding strength of fibers themselves is applied in the thickness direction and thus the resultant nonwoven fabric is suppressed, even when being applied with an external pressure, from having a reduced volume. The fiber having a spiral shape in particular allows the resultant nonwoven fabric applied with an external pressure to easily have an original shape. Thus, even when the volume is slightly reduced due to an excessive external pressure, such a spiral shape can easily have an original thickness when the external pressure is cancelled.

The term "visible crimp fiber" is a collective term denoting previously crimped fibers (e.g., fibers shaped by a machine crimp, the ones having a core-in-sheath structure of an eccentric core type, the side-by-side type). The term "latent crimp fiber" means fibers that are crimped when heated.

In a machine crimp, the appearance of crimp in a continuous straight fiber after a fiber spinning can be controlled by the difference in the circumferential velocity of a line speed, heat, or pressurization. As the number of crimps per a unit length is higher, a yielding strength under an external pressure can be increased. For example, the number of crimps is 10 to 35/inch or preferably 15 to 30/inch.

Fibers shaped by heat shrinkage are composed of two or more resins having different melting points. When such fibers are heated, the difference in the melting point causes a change in a heat shrinkage rate to cause a three-dimensional crimping of the fibers. A complex shape of a cross section of a fiber includes the core-in-sheath structure of an eccentric core type or the side-by-side type in which left and right components have different melting points for example. Such fibers exemplarily have a heat shrinkage rate of, for example, 5 to 90% or preferably 10 to 80%.

A heat shrinkage rate can be measured based on the following method.

(1) A web of 200 g/m$^2$ is prepared by 100% of fiber to be measured.

(2) A sample cut to have a size of 250×250 mm is prepared.

(3) This sample is left in an oven at 145 degrees C. (418.15K) for 5 minutes.

(4) The length after shrinkage is measured.

(5) The heat shrinkage rate is measured based on the difference in length before and after the heat shrinkage.

When this nonwoven fabric is used as a surface sheet, the nonwoven fabric preferably has a fineness of 1.1 to 8.8 dtex in consideration of liquid permeation or texture, for example.

When this nonwoven fabric is used as a surface sheet, the fiber assembly may be composed of fibers such as, in order to absorb even a small amount of menstrual blood or sweat left on skin for example, cellulose-base hydrophilic fibers (e.g., pulp, chemical pulp, rayon, acetate, natural cotton). However, cellulose-base fibers difficultly discharge liquid once absorbed therein. Thus, cellulose-base fibers may be preferably mixed in a range from 0.1 to 5 mass % to the entire mixture for example.

When this nonwoven fabric is used as a surface sheet, the above-described hydrophobic synthetic fibers may be mixed with hydrophilic agent or water repellent agent or the like or may be coated in consideration of liquid permeation or rewet back for example. Alternatively, the nonwoven fabric also may be subjected to a corona processing or plasma processing to provide a hydrophilic property. Alternatively, the nonwoven fabric also may include water-repellent fibers. The term "water-repellent fibers" herein means fibers subjected to a known water-repellent processing.

In order to provide whiter nonwoven fabric, the nonwoven fabric also may include, for example, inorganic filler (e.g., titanium oxide, barium sulfate, calcium carbonate). When the nonwoven fabric uses the core-in-sheath type complex fibers, such filler may be included only in the core or in both of the core and the sheath.

As described above, a fiber web in which fibers can be easily re-arranged by airflow is a fiber web having a relatively long fiber that is made by the card method. In order to provide nonwoven fabric by forming groove portions (concavities and convexities) by a plurality of air flows to subsequently retain the shapes, the through air method is preferred according to which a fiber assembly is heated by an oven processing (heat processing) to heat-seal thermoplastic fibers. Fibers suitable for this manufacture method are preferably those having the core-in-sheath structure or side-by-side structure in order to heat-seal intersecting points of the fibers or are more preferably those having the core-in-sheath structure in which sheaths can be easily heat-sealed in a secure manner. In particular, core-in-sheath complex fibers consisting of polyethylene terephthalate and polyethylene or core-in-sheath complex fibers consisting of polypropylene and polyethylene are preferred. These fibers may be separately used or two or more types of fibers also may be combined. These fibers preferably have a fiber length of 20 to 100 mm or more preferably 35 to 65 mm.

5-2. Manufacture Apparatus of Nonwoven Fabric 5-2-1. Fluid Mainly Consisting of Gas Fluid mainly consisting of gas of the present invention exemplarily may be, for example, gas adjusted at a room temperature or a predetermined temperature or aerosol in which the gas includes solid substance or liquid fine particles.

Gas exemplarily may be, for example, air or nitrogen. Gas includes moisture from liquid (e.g., water vapor).

Aerosol means gas in which liquid or solid substance is dispersed including, for example, ink for coloration, softener for improving softness (e.g., silicon), hydrophilic property or water-repellent active agent for an antistatic purpose or for controlling a wetting property, inorganic filler (e.g., titanium oxide, barium sulfate) for improving a fluid energy, powder bond (e.g., polyethylene) for improving a fluid energy and for more securely maintaining the shape, in a heat processing, of concavities and convexities, antihistamine agent for itching prevention (e.g., diphenhydramine hydrochloride, isopropyl methyl phenol), moisturizing agent, or disinfectant. Solid substance herein means to include the gel-like one.

The temperature of fluid, mainly consisting of gas, can be appropriately adjusted depending on the property of fibers constituting the fiber assembly or the shape of a to-be-manufactured nonwoven fabric.

In order to move fibers constituting a fiber assembly in a favorable manner for example, a certain level of high temperature of fluid, mainly consisting of gas, is preferred because it increases the degree of freedom of the fibers constituting the fiber assembly. When a fiber assembly includes thermoplastic fibers, fluid, mainly consisting of gas, can have a temperature at which the thermoplastic fiber can be softened so that thermoplastic fibers placed in a region blown with the fluid, mainly consisting of gas, for example can be softened or melt and can be subsequently cured again.

By the temperature as described above, the shape of nonwoven fabric is retained when being blown with fluid, mainly consisting of gas, for example. The above temperature also provides strength to a fiber assembly (nonwoven fabric) to prevent, when the fiber assembly is moved by a predetermined transportation means, the fiber assembly from being broken.

The flow rate of the fluid, mainly consisting of gas, can be appropriately adjusted. Specific examples of a fiber assembly in which fibers have a degree of freedom to one another include, for example, the fiber web 100 mainly having the core-in-sheath fibers in which the sheath has high density polyethylene and the core has polyethylene terephthalate, the fiber length is 20 to 100 mm or preferably 35 to 65 mm, the fineness is 1.1 to 8.8 dtex or preferably 2.2 to 5.6 dtex that has a fiber length of 20 to 100 mm or preferably 35 to 65 mm when using spread fiber by the card method or has a fiber length of 1 to 50 mm or preferably 3 to 20 mm when using spread fiber by the air-laid method. The fiber web 100 can be exemplarily adjusted to achieve 10 to 1000 g/m$^2$ or preferably 15 to 100 g/m$^2$. Fluid, mainly consisting of gas, may be blown to the fiber web 100, for example, through the blowing unit 910 (blowing opening 913: diameter of 0.1 to 30 mm or preferably 0.3 to 10 mm: pitch of 0.5 to 20 mm or preferably 3 to 10 mm: shape of a circle, an elliptic, or a rectangular shape) including the plurality of blowing openings 913 shown in FIG. 8 or FIG. 9 to blow hot air having a temperature or 15 to 300 degrees C. (288.15K to 573.15K) or preferably 100 to 200 degrees C. (373.15K to 473.15K) with an air volume of 3 to 50 [L/(minute·hole)] or preferably 5 to 20 [L/(minute·hole)]. When fluid, mainly consisting of gas, is blown based on the above conditions for example, such a fiber assembly is preferred as a fiber assembly of the present invention in which constituting fibers can have a different position or direction. By preparing the fiber assembly based on fiber and manufacture conditions as described above, the nonwoven fabric shown in FIGS. 2 and 3 for example can be formed. The groove portion 1 or the convex portion 2 can have a size or a fiber basis weight of web in the following range. The groove portion 1 may have a thickness of 0.05 to 10 mm or preferably 0.1 to 5 mm, a width of 0.1 to 30 mm or preferably 0.5 to 5 mm, and a fiber basis weight of web of 2 to 900 g/m$^2$ or preferably 10 to 90 g/m$^2$. The convex portion 2 may have a thickness of 0.1 to 15 mm or preferably 0.5 to 10 mm, a width of 0.5 to 30 mm or preferably 1.0 to 10 mm, and a fiber basis weight of web of 5 to 1000 g/m$^2$ or preferably 10 to 100 g/m$^2$. Although the nonwoven fabric can be prepared by values within the above range, the invention is not limited to this range.

5-2-2. Air Permeable Supporting Member

The air permeable supporting member 200 may exemplarily be a supporting member in which a face supporting the fiber web 100 has a substantially flat surface or a substantially curved surface and a surface in the substantially flat surface or the substantially curved surface is substantially flat. The substantially flat surface or substantially curved surface may exemplarily include, for example, a plate-like shape or a circular cylinder-like shape. The substantially flat shape may mean, for example, a surface in the supporting member on which the fiber web 100 is placed does not have concavities and convexities for example. Specifically, the supporting member may exemplarily be the one in which a mesh in the mesh supporting member 210 does not include concavities and convexities for example.

This air permeable supporting member may exemplarily be, for example, a plate-like supporting member or a circular cylinder-like supporting member. Specifically, the above-described mesh supporting member 210 or supporting member 270 may exemplarily be used.

The air permeable supporting member 200 can be detachably placed in the nonwoven fabric manufacture apparatus 90. Thus, the air permeable supporting member 200 depending on a desired nonwoven fabric can be appropriately placed. In other words, in the nonwoven fabric manufacture apparatus 90, the air permeable supporting member 200 can be exchanged with another air permeable supporting member selected from among a plurality of different air permeable supporting members.

The following section will describe the mesh supporting member 210 shown in FIG. 4 and the supporting member 270 in FIG. 16. This air permeable mesh part may exemplarily be, for example, a air permeable net obtained by using thread by resin (e.g., polyester, polyphenylene sulfide, nylon, conductive monofilament) or thread by metal (e.g., stainless, copper, aluminum) and being woven into plain weave, diagonal weave, sateen weave, double cloth, or spiral knitted for example.

The air permeable net has an air permeability that can be partially changed, for example, by partially changing a knitting method, the thickness of a thread, or the shape of a thread. Specifically, this air permeable net may exemplarily be a spiral-knitted air permeable mesh made by polyester, or a spiral knitted air permeable mesh made by stainless by a flat thread and a circular thread.

As a plate-like supporting member, a sleeve made of metal (e.g., stainless, copper, aluminum) may be exemplarily used. A sleeve may exemplarily be the one obtained by partially cutting the above metal plate by a predetermined pattern. A part from which this metal is cut off functions as a pervious section, and a part from which this metal is not cut off functions as an impervious section. As described above, an impervious section preferably has a smooth surface in order to improve the slipping property of the surface.

A sleeve may exemplarily be, for example, a stainless sleeve having a thickness of 0.3 mm obtained by cutting the metal to provide hole sections arranged with an interval of 2 mm in the line flow direction (moving direction) and an interval of 3 mm in the width direction to provide a lattice-like pattern. Each of the hole sections is shaped in a rectangular with rounded corners extending in the lateral direction having a length of 3 mm and a width of 40 mm.

Alternatively, a sleeve in which hole sections are arranged in a staggered manner also may be exemplarily used. For example, a stainless sleeve having a thickness of 0.3 mm may be exemplarily used in which circular hole sections having a diameter 4 mm obtained by cutting off metal are arranged in the line flow direction (moving direction) with a pitch of 12 mm and a pitch of 6 mm in the width direction to draw a staggered pattern. As described above, a pattern to be cut off (hole sections to be formed) or the arrangement can be appropriately determined.

Furthermore, the mesh supporting member 260 shown in FIG. 12 including a predetermined undulating shape can be exemplarily used. For example, an air permeable supporting member exemplarily used that has parts that are not directly blown with fluid, mainly consisting of gas, are alternately provided to draw an undulating pattern in the line flow direction (moving direction) (e.g., wave-like pattern). By using the mesh supporting member 260 having the shape as described above, such nonwoven fabric can be obtained for example in which predetermined opening sections are formed and projections are alternately provided in the entire mesh supporting member 260 (e.g., wave-like pattern).

5-2-3. Blowing Means

By providing the blowing unit 910 to be able to change the direction of fluid, mainly consisting of gas, an interval between concave portions (groove portions) of the resultant concavities and convexities or the height of the convex portion can be appropriately adjusted for example. By providing the blowing unit 910 to be able to automatically change the direction of the fluid for example, groove portions or the like can be appropriately adjusted to provide a meander pattern (wave-like pattern, zigzag pattern) or another pattern. By adjusting a blowing amount or a blowing time of fluid mainly consisting of gas, the shape or pattern of the groove portions or opening sections can be appropriately adjusted. Fluid, mainly consisting of gas, may be blown to the fiber web 100 in a longitudinal direction, with a predetermined angle inclined to the line flow direction in the moving direction F of the fiber web 100, or with a predetermined angle opposite to the line flow direction.

5-2-4. Heating Means

In the nonwoven fabric 170 including predetermined opening sections, the fiber 101 can be adhered by, for example, the needle punch method, the span lace method, or the solvent welding method or can be thermal-adhered by the point bond method or the air through method. However, in order to maintain the shape of a predetermined opening section, the air through method is preferred. For example, a thermal processing by the air through method by the heater unit 950 is preferred.

5-2-5. Others

The nonwoven fabric manufactured by being heated by the heater unit 950 is moved by the conveyer 930 and the subsequent conveyer 940 in the predetermined direction F to a step for cutting or winding the nonwoven fabric to have a predetermined shape for example. The conveyer 940 also may include the belt unit 949 and the rotation section 941 for example as in the conveyer 930.

What is claimed is:

1. A nonwoven fabric, comprising:
   a plurality of low basis weight portions longitudinally extending in a first direction and being formed by directing a fluid to a fiber assembly; and
   a plurality of high basis weight portions longitudinally extending in the first direction, said low basis weight portions and high basis weight portions being alternately arranged adjacent to each other, each of the high basis weight portions has a central portion and side portions on opposite sides of the central portion;
   wherein
   a fiber basis weight of each of the low basis weight portions is less than a fiber basis weight of each of the high basis weight portions;
   in each of the low basis weight portions, a content percentage of fibers oriented in a second direction that is perpendicular to the first direction is greater than a content percentage of fibers oriented in the first direction;
   in each of the high basis weight portions, a content percentage of fibers oriented in a thickness direction of the fabric is greater than that in each of the low basis weight portions; and
   a content percentage of fibers oriented in the first direction in each of the side portions is greater than that in the central portion.

2. The nonwoven fabric according to claim 1, wherein a fiber density of each of the low basis weight portions is less than a fiber density of each of the high basis weight portions.

3. The nonwoven fabric according to claim 1, wherein
   the low basis weight portions are respectively a plurality of groove portions recessed in the thickness direction of the nonwoven fabric on a first surface side of the nonwoven fabric, and
   the high basis weight portions are a plurality of convex portions projected in the thickness direction from a first surface side.

4. The nonwoven fabric according to claim 3, wherein the fiber basis weight of each of the groove portions is no greater than 90% of the fiber basis weight of each of the convex portions.

5. The nonwoven fabric according to claim 4, wherein the fiber basis weight of each of the groove portions is 3 g/m² to 200 g/m², and the basis weight of each of the convex portions is 15 g/m² to 250 g/m².

6. The nonwoven fabric according to claim 5, wherein a fiber density of each of the convex portions is no greater than 0.20g/cm³, and a fiber density of each of the groove portions is no greater than 0.18g/cm³.

7. The nonwoven fabric according to claim 3, wherein a height of each of the groove portions in the thickness direction is no greater than 90% of a height of the convex portion.

8. The nonwoven fabric according to claim 3, wherein each of the groove portions has a plurality of areas with fiber basis weights that are less than an average fiber basis weight in a bottom of said groove portion.

9. The nonwoven fabric according to claim 8, wherein each of the areas is an opening extending through an entire thickness of the fabric.

10. The nonwoven fabric according to claim 9, wherein fibers positioned at a peripheral edge of each of the openings are oriented along the peripheral edge.

11. The nonwoven fabric according to claim 3, wherein the adjacent convex portions, between which one of the groove portions is sandwiched, have different heights in the thickness direction.

12. The nonwoven fabric according to claim 3, wherein a top of each of the convex portions is substantially flat.

13. The nonwoven fabric according to claim 3, wherein the fabric comprises, on a second surface side opposite to the first surface side, a plurality of areas projecting in a direction opposite to the projecting direction of the convex portions.

14. The nonwoven fabric according to claim 3, wherein the nonwoven fabric is undulating in the first direction.

15. The nonwoven fabric according to claim 3, wherein the fabric on a second surface side opposite to the first surface side is substantially flat.

16. The nonwoven fabric according to claim 1, wherein the nonwoven fabric is undulating in the first direction.

17. The nonwoven fabric according to claim 1, wherein fibers constituting the fiber assembly include water-repellant fibers.

18. The nonwoven fabric according to claim 1, wherein
   in each of the high basis weight portions, the content percentage of the fibers oriented in the thickness direction of the central portion is greater than that of each of the side portions.

19. A nonwoven fabric, comprising:
   a plurality of low basis weight portions longitudinally extending in a first direction and being formed by directing a fluid to a fiber assembly; and
   a plurality of high basis weight portions longitudinally extending in the first direction, said low basis weight portions and high basis weight portions being alternately arranged adjacent to each other, each of the high basis weight portions has a central portion and side portions on opposite sides of the central portion;
   wherein
   a fiber basis weight of each of the low basis weight portions is less than a fiber basis weight of each of the high basis weight portions;
   in each of the low basis weight portions, a content percentage of fibers oriented in a second direction that is perpendicular to the first direction is greater than a content percentage of fibers oriented in the first direction;
   the central portion of each of the high basis weight portions has a content percentage of fibers oriented in a thickness direction of the fabric greater than that in each of the low basis weight portions; and
   the side portions include fibers, which are oriented in the first direction and have been moved, by said fluid directed to said fiber assembly, from adjacent low basis weight portions to said side portions, and therefore the side portions have a content percentage of the fibers oriented in the first direction greater than that of the central portion.

* * * * *